United States Patent
Cole

(10) Patent No.: US 10,889,576 B2
(45) Date of Patent: *Jan. 12, 2021

(54) PHTHALAZINONE COMPOUNDS AND METHODS FOR THE TREATMENT OF CYSTIC FIBROSIS

(71) Applicant: FLATLEY DISCOVERY LAB, LLC, Charlestown, MA (US)

(72) Inventor: Bridget M. Cole, Quincy, MA (US)

(73) Assignee: Flatley Discovery Lab, LLC, Charlestown, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/398,680

(22) Filed: Apr. 30, 2019

(65) Prior Publication Data

US 2019/0256505 A1 Aug. 22, 2019

Related U.S. Application Data

(63) Continuation of application No. 15/615,466, filed on Jun. 6, 2017, now Pat. No. 10,280,160, which is a
(Continued)

(51) Int. Cl.

| C07D 413/12 | (2006.01) |
|---|---|
| A61K 31/502 | (2006.01) |
| A61P 11/00 | (2006.01) |
| A61K 45/06 | (2006.01) |
| C07D 413/14 | (2006.01) |
| C07D 498/04 | (2006.01) |
| A61K 31/38 | (2006.01) |
| A61K 31/4245 | (2006.01) |
| A61K 31/443 | (2006.01) |
| A61K 31/47 | (2006.01) |
| A61K 31/5025 | (2006.01) |
| A61K 31/506 | (2006.01) |
| A61K 31/519 | (2006.01) |
| C07D 237/32 | (2006.01) |
| C07D 401/04 | (2006.01) |
| C07D 401/06 | (2006.01) |
| C07D 405/04 | (2006.01) |
| C07D 405/12 | (2006.01) |
| C07D 405/14 | (2006.01) |
| C07D 487/04 | (2006.01) |
| A61K 31/5377 | (2006.01) |
| C07D 401/12 | (2006.01) |

(Continued)

(52) U.S. Cl.
CPC ............ *C07D 413/12* (2013.01); *A61K 31/38* (2013.01); *A61K 31/4245* (2013.01); *A61K 31/443* (2013.01); *A61K 31/47* (2013.01); *A61K 31/502* (2013.01); *A61K 31/506* (2013.01); *A61K 31/5025* (2013.01); *A61K 31/519* (2013.01); *A61K 31/5377* (2013.01); *A61K 45/06* (2013.01); *A61P 11/00* (2018.01); *C07D 237/32* (2013.01); *C07D 401/04* (2013.01); *C07D 401/06* (2013.01); *C07D 401/12* (2013.01); *C07D 401/14* (2013.01); *C07D 403/04* (2013.01); *C07D 405/04* (2013.01); *C07D 405/12* (2013.01); *C07D 405/14* (2013.01); *C07D 413/14* (2013.01); *C07D 417/14* (2013.01); *C07D 487/04* (2013.01); *C07D 495/14* (2013.01); *C07D 498/04* (2013.01); *C07D 519/00* (2013.01)

(58) Field of Classification Search
None
See application file for complete search history.

(56) References Cited

U.S. PATENT DOCUMENTS

| 4,665,181 A | 5/1987 | Radov et al. |
| 5,668,279 A | 9/1997 | Chakravarty et al. |

(Continued)

FOREIGN PATENT DOCUMENTS

| DE | 286354 A5 | 1/1991 |
| EP | 0634404 A1 | 1/1995 |

(Continued)

OTHER PUBLICATIONS

CAS 53704-87-3 STN: Nov. 16, 1984.
(Continued)

*Primary Examiner* — Eric Olson
(74) *Attorney, Agent, or Firm* — Elmore Patent Law Group, P.C.; Edgar W. Harlan; Carolyn S. Elmore

(57) ABSTRACT

The invention relates to a compound of Formula I and methods of treating CFTR (cystic fibrosis transmembrane conductance regulator) mediated diseases, in particular cystic fibrosis, comprising the step of administering a therapeutically effective amount of a compound of Formula I to a patient in need thereof:

Formula I

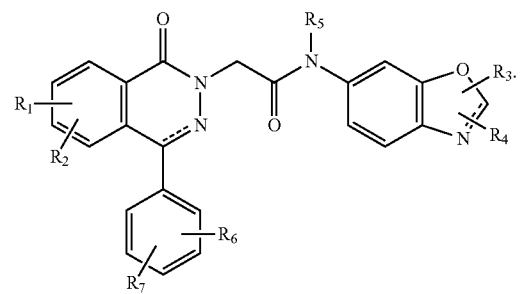

6 Claims, No Drawings

Related U.S. Application Data continuation of application No. 14/599,998, filed on Jan. 19, 2015, now Pat. No. 9,682,969, which is a continuation of application No. 14/210,261, filed on Mar. 13, 2014, now Pat. No. 8,937,178.

(60) Provisional application No. 61/778,870, filed on Mar. 13, 2013.

(51) Int. Cl.
  *C07D 401/14*  (2006.01)
  *C07D 403/04*  (2006.01)
  *C07D 417/14*  (2006.01)
  *C07D 495/14*  (2006.01)
  *C07D 519/00*  (2006.01)

(56) References Cited

U.S. PATENT DOCUMENTS

| | | | |
|---|---|---|---|
| 6,103,718 | A | 8/2000 | Sterk |
| 6,180,629 | B1 | 1/2001 | Wang et al. |
| 6,255,303 | B1 | 7/2001 | Sterk et al. |
| 6,498,160 | B2 | 12/2002 | Napoletano et al. |
| 6,544,993 | B1 | 4/2003 | Sterk et al. |
| 6,924,284 | B2 | 8/2005 | Beaton et al. |
| 7,186,710 | B2 | 3/2007 | Sterk et al. |
| 7,432,263 | B2 | 10/2008 | Pulici et al. |
| 7,470,688 | B2 | 12/2008 | Javaid et al. |
| 8,129,401 | B2 | 3/2012 | Gharat et al. |
| 8,937,178 | B2 | 1/2015 | Cole |
| 9,012,443 | B2 | 4/2015 | Boezio et al. |
| 9,682,969 | B2 | 6/2017 | Cole |
| 9,783,529 | B2 | 10/2017 | Cole et al. |
| 9,790,215 | B2 | 10/2017 | Cole et al. |
| 10,280,160 | B2 | 5/2019 | Cole |
| 10,370,366 | B2 | 8/2019 | Cole |
| 2003/0105328 | A1 | 6/2003 | Strehlke et al. |
| 2004/0192695 | A1 | 9/2004 | Petrov et al. |
| 2008/0161280 | A1 | 7/2008 | Gandhi et al. |
| 2008/0286204 | A1 | 11/2008 | Hadida-Ruah et al. |
| 2009/0163545 | A1 | 6/2009 | Goldfarb et al. |
| 2011/0105509 | A1 | 5/2011 | Kaila et al. |

FOREIGN PATENT DOCUMENTS

| | | |
|---|---|---|
| EP | 0934933 A1 | 8/1999 |
| JP | 56-061365 A | 5/1981 |
| JP | 2012-020961 A1 | 2/2012 |
| WO | 9410151 A1 | 5/1994 |
| WO | 9838168 A1 | 9/1998 |
| WO | 02036576 A1 | 5/2002 |
| WO | 02066437 A1 | 8/2002 |
| WO | 2006034419 A2 | 3/2006 |
| WO | 2008019292 A2 | 2/2008 |
| WO | 2009/019598 A2 | 2/2009 |
| WO | 2009123870 A1 | 10/2009 |
| WO | 2009124167 A1 | 10/2009 |

OTHER PUBLICATIONS

CAS 902567-16-2, STN: Aug. 18, 2016.
CAS 902598-47-4.
CAS RN 1115930-01-2, STN Entry Date Mar. 5, 2009.
CAS RN 1115976-21-0, STN Entry Date Mar. 5, 2009.
CAS RN 1116070-76-8, STN Entry Date Mar. 5, 2009.
CAS RN 1118853-08-9, STN Entry Date Mar. 11, 2009.
CAS RN 1214400-23-3, STN Entry Date Mar. 25, 2010.
CAS RN 1251694-86-6, STN Entry Date Nov. 3, 2010.
CAS RN 1324990-51-3, STN Entry Date Aug. 29, 2011.
CAS RN 1325474-52-9, STN Entry Date Aug. 30, 2011.
CAS RN 1356731-74-2, STN Entry Date Feb. 14, 2012.
CAS RN 1357902-01-2, STN Entry Date Feb. 28, 2012.
CAS RN 1359474-16-0, STN Entry Date Mar. 2, 2012.
CAS RN 1387400-35-2, STN Entry Date Aug. 7, 2012.
CAS RN 364612-60-2, STN Entry Date Oct. 25, 2001.
CAS RN 364612-61-3, STN Entry Date Oct. 25, 2001.
CAS RN 684234-59-1, STN Entry Date May 21, 2004.
CAS RN 695200-56-7, STN Entry Date Jun. 18, 2004.
CAS RN 702647-29-8, STN Entry Date Jul. 2, 2004.
CAS RN 736965-46-1, STN Entry Date Sep. 1, 2004.
CAS RN 799811-17-9, STN Entry Date Dec. 20, 2004.
CAS RN 840463-36-7, retrieved from www.chemspider.com/ Chemical Structure.
CAS RN 840463-50-5, STN Entry Date Mar. 2, 2005.
CAS RN 896073-38-4, STN Entry Date Jul. 25, 2006.
CAS RN 896594-33-5, STN Entry Date Jul. 28, 2006.
CAS RN 896815-44-4, STN Entry Date Jul. 28, 2006.
CAS RN 896830-26-5, STN Entry Date Jul. 28, 2006.
CAS RN 899386-28-8, STN Entry Date Aug. 7, 2006.
CAS RN 902165-32-6, STN Entry Date Aug. 17, 2006.
CAS RN 902499-72-3, STN Entry Date Aug. 17, 2006.
CAS RN 902499-88-1, STN Entry Date Aug. 17, 2006.
CAS RN 902500-40-7, STN Entry Date Aug. 17, 2006.
CAS RN 902500-57-6, STN Entry Date Aug. 17, 2006.
CAS RN 902596-62-7, STN Entry Date Aug. 18, 2006.
CAS RN 902597-18-6, STN Entry Date Aug. 18, 2006.
CAS RN 902597-26-6, STN Entry Date Aug. 18, 2006.
CAS RN 913687-55-5, STN Entry Date Nov. 21, 2006.
CAS RN 920677-37-8, STN Entry Date Feb. 13, 2007.
CAS RN 920684-42-0, STN Entry Date Feb. 13, 2007.
CAS RN 920726-70-1, STN Entry Date Feb. 13, 2007.
CAS RN 930018-50-1, STN Entry Date Apr. 13, 2007.
CAS RN 931685-00-6, STN Entry Date Apr. 22, 2007.
CAS RN 902165-28-0, STN Entry Date Aug. 17, 2006.
CAS RN 902164-83-4, STN Entry Date Aug. 17, 2006.
CAS RN 902596-35-4, STN Entry Date Aug. 18, 2006.
CAS RN 664978-35-2, STN Entry Date Mar. 19, 2004.
CAS RN 1251574-92-1, STN Entry Date Nov. 3, 2010.
CAS RN 1061505-98-3, STN Entry Date Oct. 15, 2008.
"2(1H)-Phthalazineacetamide, N-1,3-benzodioxo1-5-y1-4-(2,5-dimethylphenyl)-1-oxo-", Chemical Abstracts Registry entry #920811-87-6, entered into STN on Feb. 14, 2007, downloaded from STN file Registry, Feb. 14, 2007.
Abd Alla, M. S. et al., "Synthesis and anti-inflammatory Evaluation of Some Condensed [4-(3-4-dimethylphenyl)-1(2H)-oxo-phthalazin 2-yl) Acetic Acid Hydrazide", European J. of Medicinal Chem., 45(4), 2010, 1267-1277.
Bayoumy, B. et al., "Synthesis of Some Newer Oxadiazolo-, Oxadiazolino-, Thiadiazolo-, and Triazolothiadiazino-phthalazinone Derivatives", Egyptian Journal of Chemistry, 33(3), Claims: 1-5, 11-12, 16-17, 1990, 267-275.
Bobova, T. A. et al., "Alkylation of 4-R-substituted-2H-phthalazin-1-ones" Izvestiya Vysshikh Uchebnykh Zavedenii, Khimiya i Khimicheskaya Tekhnologiya, 54(11), 2011, 41-43.
Capelli, A. M. et al., "Identification of novel Alpha17 nAChR positive allosteric modulators with the use of pharmacophore in silico screening methods", Bioorganic & Medicinal Chemistry Letters, 20(15): Jun. 8, 2010, 4561-4565.
Cohen-Cymberknoh, M. et al., "Concise Clinical Review. Managing Cystic Fibrosis: Strategies That Increase Life Expectancy and Improve Quality of Life", Am J Respir Grit Care Med, 183: 2011, 1463-1471.
Cuthbert, A.W. "Review: New horizons in the treatment of cystic fibrosis", British Journal of Pharmacology, 163: 2010, 173-183.
Deeb, O. et al., "Exploring QSARs for Inhibitory Activity of Non-peptide HIV-1 Protease Inhibitors by GA-PLS and GA-SVM", Chem Biol Drug Des; vol. 75, 2010, 506-514.
Demirayak, S. et al., "Some pyridazinone and phthalazinone derivatives and their vasodilator activities", Arch Pharm Res, 27(1): Jan. 2004, 13-8.
Devor, D.C. et al., "Pharmacological modulation of ion transport across wildtype and tiF508 CFTR-expressing human bronchial epithelia", Am J Physiol Cell Physiol, 279: 2000, C461-C479.

(56) References Cited

OTHER PUBLICATIONS

El-Hashash, M. et al., "Synthesis and Antimicrobial Activity of Some Condensed [4-(2,4,6-Trimethylphenyl)-1(2H)-oxo-phthalazin-2-yl]acetic Acid Hydrazide", Chin. J. Chem., 30: Jan. 19, 2012, 616-626.
Ettmayer, P. et al., "Lessons Learned from Marketed and Investigational Prodrugs", Journal of Medicinal Chemistry, 47(10), May 6, 2004, 2393-2404.
Horn, et al., STN International HCAPLUS database, (Columbus, Ohio), Accession No: 408820, RN 132544-94-6, 1991.
Kassab, E. A. et al., "Synthesis and Behaviour of 4-(4'-Chloro-3'-Methyl Phenyl)-1(2H)-Phthalazinone Towards Certain Electrophiles and Nucleophiles", Egypt. J. Chem., 48(2), 2005, 183-199.
Kolobov, A. V. et al., "6-Aryl-2H-pyridazin-3-ones and 4-aryl-5,6,7,8-tetrahydro-2Hphthalazine-1-ones: synthesis and N-alkylation reactions", Izvestiya Vysshikh Uchebnykh Zavedenii, Khimiya i Khimicheskaya Tekhnologiya (2006), 49(3), 2006, 24-28.
Macchiarulo, et al., "QSAR Study of Anticonvulsant Negative Allosteric Modulators of the AMPA Receptor", Journal of Medicinal Chemistry vol. 47, 2004, 1860-1863.
Mohamed, F. K. et al., "Synthesis, reactions and antimicrobial activity on some novel phthalazinone derivatives", Der Pharma Chemica, 2(3): http://derpharmachemica.com/archive.html, 2010, 267-276.
Mohamed, F. K. et al., "Synthesis, reactions and antimicrobial activity on some novel phthalazinones derivatives", Der Chemica Sinica, 1(1): www.pelagiaresearchlibrary.com, 2010, 20-31.
Mohamed, F. K. "Synthesis, Reactions, and Antimicrobial Activity on Some Novel Phthalazinone Derivatives", Egyptian Journal of Chemistry, 53(5): 2010, 645-660.
Sequra-Cabrera, A. et al., "Integrative computational protocol for the discovery of inhibitors of the Helicobacter pylori nickel response regulator (NikR)", J Mol Model, 17: Mar. 1, 2011, 3075-3084.
Silverman, R. B. "Prodrugs and Drug Delivery Systems", The Organic Chemistry of Drug Design and Drug Action. Published by Academic Press, 1992, 352-397.
Stella, V. J. "Prodrugs as Therapeutics", Expert Opinion on Therapeutic Patents, 14(3): 2004, 277-280.
Sui, J. et al., "Optimization of a Yellow Fluorescent Protein-Based Iodide Influx High-Throughput Screening Assay for 6 Cystic Fibrosis Transmembrane Conductance Regulator (CFTR) Modulators", Assay and Drug Development Technologies, 8(6): Dec. 2010, 1-15.
Testa, B. "Prodrug Research: Futile or Fertile", Biochemical Pharmacology, 68: 2004, 2097-2106.
Van Der Mey, M. et al., "Synthesis and Structure-Activity Relationships of cis-Tetrahydrophthalazinone/ Pyridazinone Hybrids: A Novel Series of Potent Dual PDE3/PDE4 Inhibitory Agents", J. Med. Chem., 46, 2003, 2008-2016.
Wolff, M. E. Burger's Medicinal Chemistry and Drug Discovery, Fifth Edition, Volume 5(1): Principles and Practice published by John Wiley and Sons, 1994, 975-977.
Yassin, F. et al., "Synthesis and reactions of oxadiazolo, thiadiazolo and triazolophthalazin-1(2H)-one derivatives", Der Pharma Chemica, 4(3): online at www.derpharmachemica.com, 2012, 860-866.
Yassin, F. A. et al., "Synthesis of 4,5,6,7-Tetraphenyl-8-(substituted)-3(2H)-phthalazinone Derivatives Likely to Possess Antihypertensive Activity", Bull. Korean Chem. Soc., 11(1): 1990, 7-10.

PHTHALAZINONE COMPOUNDS AND METHODS FOR THE TREATMENT OF CYSTIC FIBROSIS

RELATED APPLICATIONS

This application is a continuation of U.S. application Ser. No. 15/615,466, filed on Jun. 6, 2017, which is a continuation of U.S. application Ser. No. 14/599,998 (now U.S. Pat. No. 9,682,969), filed on Jan. 19, 2015, which is a continuation of U.S. application Ser. No. 14/210,261 (now U.S. Pat. No. 8,937,178), filed on Mar. 13, 2014, which claims the benefit of U.S. Provisional Application No. 61/778,870, filed on Mar. 13, 2013. The entire teachings of the above applications are incorporated herein by reference.

BACKGROUND

Cystic fibrosis (CF) is a lethal, recessive, genetic disease affecting approximately 1 in 2500 live births among Caucasians. (Cohen-Cymberknoh M, Shoseyov D, Kerem E. Managing cystic fibrosis: strategies that increase life expectancy and improve quality of life. Am J Respir Crit Care Med (2011); 183: 1463-1471; Boat T F, Welsh M J and Beaudet A L. Cystic fibrosis. (1989) IN "The Metabolic Basis of Inherited Disease" (C L Scriver, A L Beaudet, W S Sly and D Valee, eds.), $6^{th}$ Ed., pp. 2649-2680. McGraw-Hill, New York). Approximately 1 in 25 persons are carriers of the genetic defect associated with the disease. The major symptoms of cystic fibrosis include chronic pulmonary disease, pancreatic exocrine insufficiency, infertility in males, and elevated sweat electrolyte levels. The symptoms are consistent with cystic fibrosis being an exocrine disorder. (Hantash F: U.S. Patent Application No. 20060057593. Method for detecting cystic fibrosis. (2004). Published Mar. 16, 2006). The CF gene codes for a cAMP/PKA-dependent, ATP-requiring, membrane-bound chloride ion channel known as CFTR (cystic fibrosis transmembrane conductance regulator), and is, generally localized to the apical membranes of many secreting epithelia and known as CFTR (cystic fibrosis transmembrane conductance regulator). There are currently over 1700 known mutations affecting CFTR, many of which give rise to a disease phenotype. Around 75% of CF alleles contain the F508del mutation in which a triplet codon has been lost, leading to a missing phenylalanine at position 508 in the protein. This altered protein fails to be trafficked to the correct location in the cell and is generally destroyed by the proteasome. The small amount that does reach the correct location functions poorly. (Cutbert A W. New horizons in the treatment of cystic fibrosis. British J Pharm, (2011), 163: 173-183).

Although CFTR functions mainly as a chloride channel, it has many other roles, including inhibition of sodium transport through the epithelial sodium channel, regulation of the outwardly rectifying chloride channel, ATP channels, intracellular vesicle transport, and inhibition of endogenous calcium-activated chloride channels. CFTR is also involved in bicarbonate-chloride exchange. A deficiency in bicarbonate secretion leads to poor solubility and aggregation of luminal mucins. Obstruction of intrapancreatic ducts with thickened secretions causes autolysis of pancreatic tissue with replacement of the body of the pancreas with fat, leading to pancreatic insufficiency with subsequent malnutrition. In the lungs, CFTR dysfunction leads to airway surface liquid (ASL) depletion and thickened and viscous mucus that adheres to airway surfaces. The result is decreased mucociliary clearance (MCC) and impaired host defenses. Dehydrated, thickened secretions lead to endobronchial infection with a limited spectrum of distinctive bacteria, mainly *Staphylococcus aureus* and *Pseudomonas aeruginosa*, Deficiency in bicarbonate secretion due to loss of CFTR function also results in a lower pH at the airway surface which impairs anti-bacterial killing activity and increases susceptibility to infection. An exaggerated inflammatory response in response to chronic lung infections leads to the development of bronchiectasis and progressive obstructive airways disease. Pulmonary insufficiency is responsible for most CF-related deaths. (Cohen-Cymberknoh M, Shoseyov D, Kerem E. Managing cystic fibrosis: strategies that increase life expectancy and improve quality of life. Am J Respir Crit Care Med (2011); 183: 1463-1471).

The prognosis for the treatment of CF has improved over the last 40 years. This was achieved by improving pancreatic enzyme supplements, drugs designed to treat pulmonary infection, reduce inflammation and enhance mucociliary clearance. Currently the therapeutic challenges are to correct the biochemical defect of CF and to identify effective treatments for chronic respiratory infection. (Frerichs C, Smyth A. Treatment strategies for cystic fibrosis: what's in the pipeline? Pharmacotherapy (2009), 10: 1191-1202).

SUMMARY

The invention relates to a compound of Formula I and methods of treating CFTR (cystic fibrosis transmembrane conductance regulator) mediated diseases, in particular cystic fibrosis, comprising the step of administering a therapeutically effective amount of a compound of Formula I to a patient in need thereof:

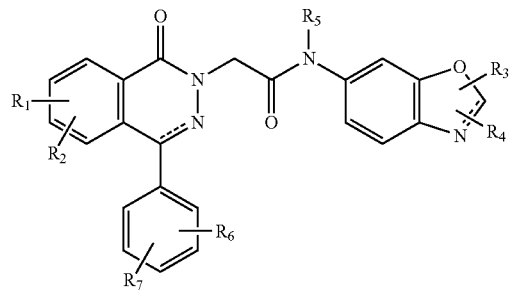

Formula I or a pharmaceutically acceptable salt, ester or prodrug thereof;

wherein ==== represents a single or double bond;

$R_1$ is selected from hydrogen, hydroxy, amino, —$C_1$-$C_8$ alkoxy, —$C_1$-$C_8$ cycloalkoxy, —$C_1$-$C_8$ alkylamino, and —$C_1$-$C_8$ dialkylamino;

$R_2$ is selected from hydrogen, halogen, $C_1$-$C_8$ alkyl, $C_2$-$C_8$ alkenyl, $C_2$-$C_8$ alkynyl, $CF_3$, —$C_1$-$C_8$ alkoxy, —$C_1$-$C_8$ alkylamino, and —$C_1$-$C_8$ dialkylamino;

$R_3$ is selected from hydrogen, $C_1$-$C_8$ alkyl, $C_2$-$C_8$ alkenyl, and $C_2$-$C_8$ alkynyl;

$R_4$ is selected from absent, hydrogen, halogen, hydroxyl, amino, $C_1$-$C_8$ alkyl, $C_2$-$C_8$ alkenyl, $C_2$-$C_8$ alkynyl, $CF_3$, $NO_2$, CN, —$C_1$-$C_8$ alkoxy, —$C_1$-$C_8$ alkylamino, and —$C_1$-$C_8$ dialkylamino;

$R_5$ is selected from $C_1$-$C_8$ alkyl, $C_2$-$C_8$ alkenyl, $C_2$-$C_8$ alkynyl, and $C_3$-$C_6$-cycloalkyl;

$R_6$ is hydrogen or halogen; and, $R_7$ is selected from hydrogen, deuterium, halogen, hydroxyl, amino, $C_1$-$C_8$ alkyl, $C_2$-$C_8$ alkenyl, $C_2$-$C_8$ alkynyl, $CF_3$, $NO_2$, CN, $C_1$-$C_8$ alkoxy, $C_1$-$C_8$ alkylamino, and $C_1$-$C_8$ dialkylamino.

DETAILED DESCRIPTION OF THE INVENTION

The invention relates to a compound of Formula I and methods of treating cystic fibrosis comprising the step of administering a therapeutically effective amount of a compound of Formula I to a patient in need thereof:

Formula I or a pharmaceutically acceptable salt, ester or prodrug thereof;

wherein ═══ represents a single or double bond;

$R_1$ is selected from hydroxy, amino, —$C_1$-$C_8$ alkoxy, —$C_1$-$C_8$ cycloalkoxy, —$C_1$-$C_8$ alkylamino, and —$C_1$-$C_8$ dialkylamino;

$R_2$ is selected from hydrogen, halogen, $C_1$-$C_8$ alkyl, $C_2$-$C_8$ alkenyl, $C_2$-$C_8$ alkynyl, $CF_3$, —$C_1$-$C_8$ alkoxy, —$C_1$-$C_8$ alkylamino, and —$C_1$-$C_8$ dialkylamino;

$R_3$ is selected from hydrogen, $C_1$-$C_8$ alkyl, $C_2$-$C_8$ alkenyl, and $C_2$-$C_8$ alkynyl;

$R_4$ is selected from absent, hydrogen, halogen, hydroxyl, amino, $C_1$-$C_8$ alkyl, $C_2$-$C_8$ alkenyl, $C_2$-$C_8$ alkynyl, $CF_3$, $NO_2$, CN, —$C_1$-$C_8$ alkoxy, —$C_1$-$C_8$ alkylamino, and —$C_1$-$C_8$ dialkylamino;

$R_5$ is selected from $C_1$-$C_8$ alkyl, $C_2$-$C_8$ alkenyl, $C_2$-$C_8$ alkynyl, and $C_3$-$C_6$-cycloalkyl;

$R_6$ is halogen; and, $R_7$ is selected from hydrogen, halogen, hydroxyl, amino, $C_1$-$C_8$ alkyl, $C_2$-$C_8$ alkenyl, $C_2$-$C_8$ alkynyl, $CF_3$, $NO_2$, CN, —$C_1$-$C_8$ alkoxy, —$C_1$-$C_8$ alkylamino, and —$C_1$-$C_8$ dialkylamino.

In one embodiment, the invention relates to a compound of Formula I wherein said compound contains a deuterium. In one embodiment, $R_5$ is selected from a $C_1$-$C_8$ alkyl, $C_2$-$C_8$ alkenyl, and $C_2$-$C_8$ alkynyl group containing one or more deuterium atoms, for example, —$CD_3$.

In one example, $R_2$ is deuterium.

In one embodiment, the invention relates to a compound of Formula:

or a pharmaceutically acceptable salt, ester or prodrug thereof;

wherein ═══ represents a single or double bond;

$R_1$ is selected from hydroxy, amino, —$C_1$-$C_8$ alkoxy, —$C_1$-$C_8$ cycloalkoxy, —$C_1$-$C_8$ alkylamino, and —$C_1$-$C_8$ dialkylamino;

$R_2$ is selected from hydrogen, halogen, $C_1$-$C_8$ alkyl, $C_2$-$C_8$ alkenyl, $C_2$-$C_8$ alkynyl, $CF_3$, —$C_1$-$C_8$ alkoxy, —$C_1$-$C_8$ alkylamino, and —$C_1$-$C_8$ dialkylamino;

$R_3$ is selected from hydrogen, $C_1$-$C_8$ alkyl, $C_2$-$C_8$ alkenyl, and $C_2$-$C_8$ alkynyl;

$R_4$ is selected from absent, hydrogen, halogen, hydroxyl, amino, $C_1$-$C_8$ alkyl, $C_2$-$C_8$ alkenyl, $C_2$-$C_8$ alkynyl, $CF_3$, $NO_2$, CN, —$C_1$-$C_8$ alkoxy, —$C_1$-$C_8$ alkylamino, and —$C_1$-$C_8$ dialkylamino;

$R_5$ is selected from $C_1$-$C_8$ alkyl, $C_2$-$C_8$ alkenyl, $C_2$-$C_8$ alkynyl, and $C_3$-$C_6$-cycloalkyl;

$R_6$ is halogen; and, $R_7$ is selected from hydrogen, halogen, hydroxyl, amino, $C_1$-$C_8$ alkyl, $C_2$-$C_8$ alkenyl, $C_2$-$C_8$ alkynyl, $CF_3$, $NO_2$, CN, —$C_1$-$C_8$ alkoxy, —$C_1$-$C_8$ alkylamino, and —$C_1$-$C_8$ dialkylamino.

The invention further relates to a compound selected from Table 1 or a pharmaceutically acceptable salt thereof:

TABLE 1

TABLE 1-continued
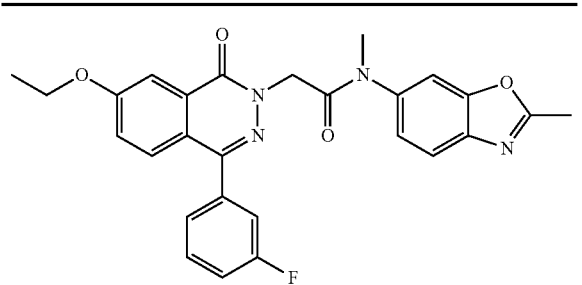
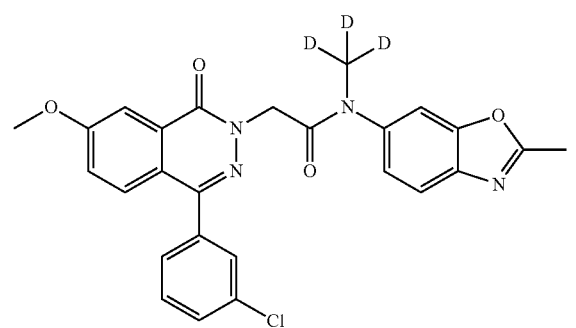
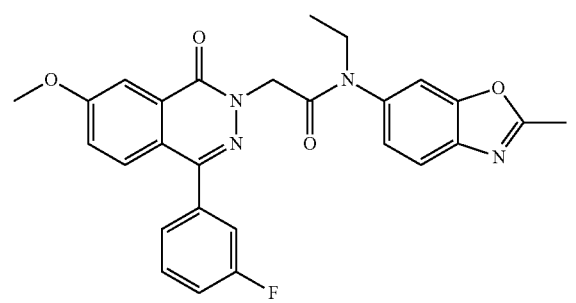
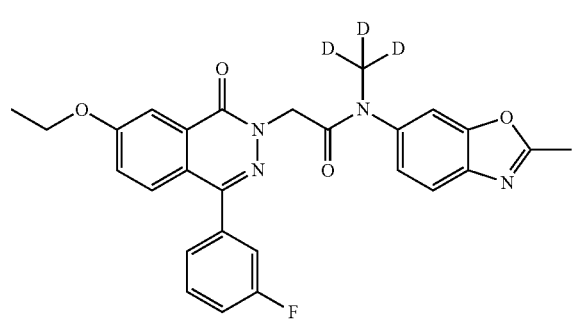 [SMILES: [2H]C([2H])([2H])N(C(=O)Cn1nc(-c2cccc(F)c2)c2ccc(OCC)cc2c1=O)c1ccc2nc(C)oc2c1]
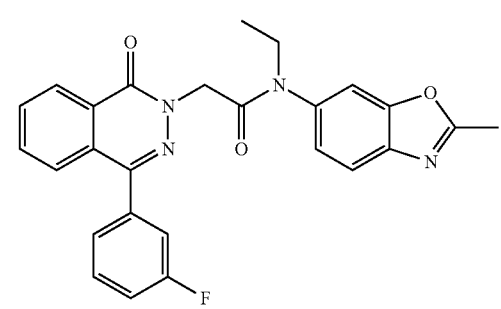 [SMILES: CCN(C(=O)Cn1nc(-c2cccc(Cl)c2)c2ccccc2c1=O)c1ccc2nc(C)oc2c1]
TABLE 1-continued
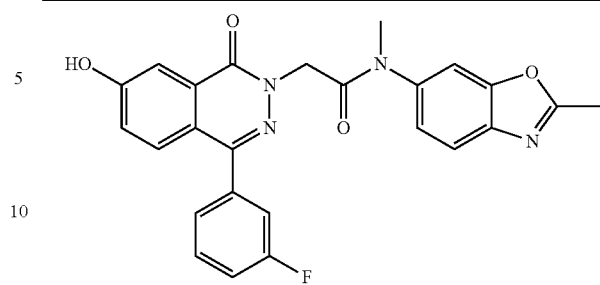
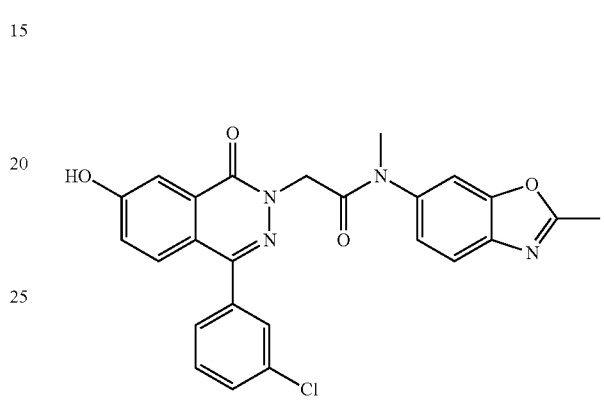
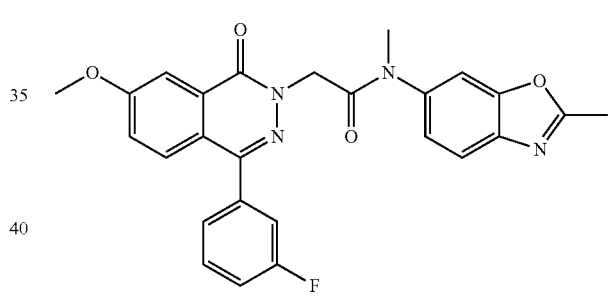
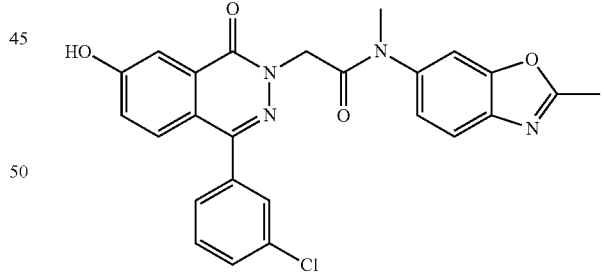
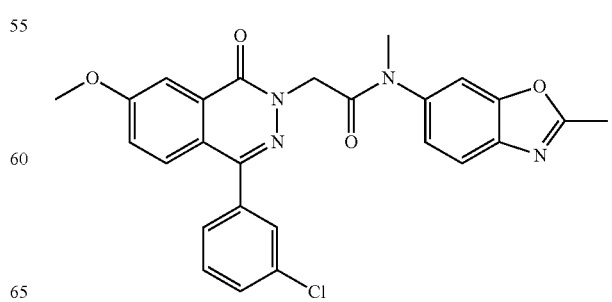

TABLE 1-continued
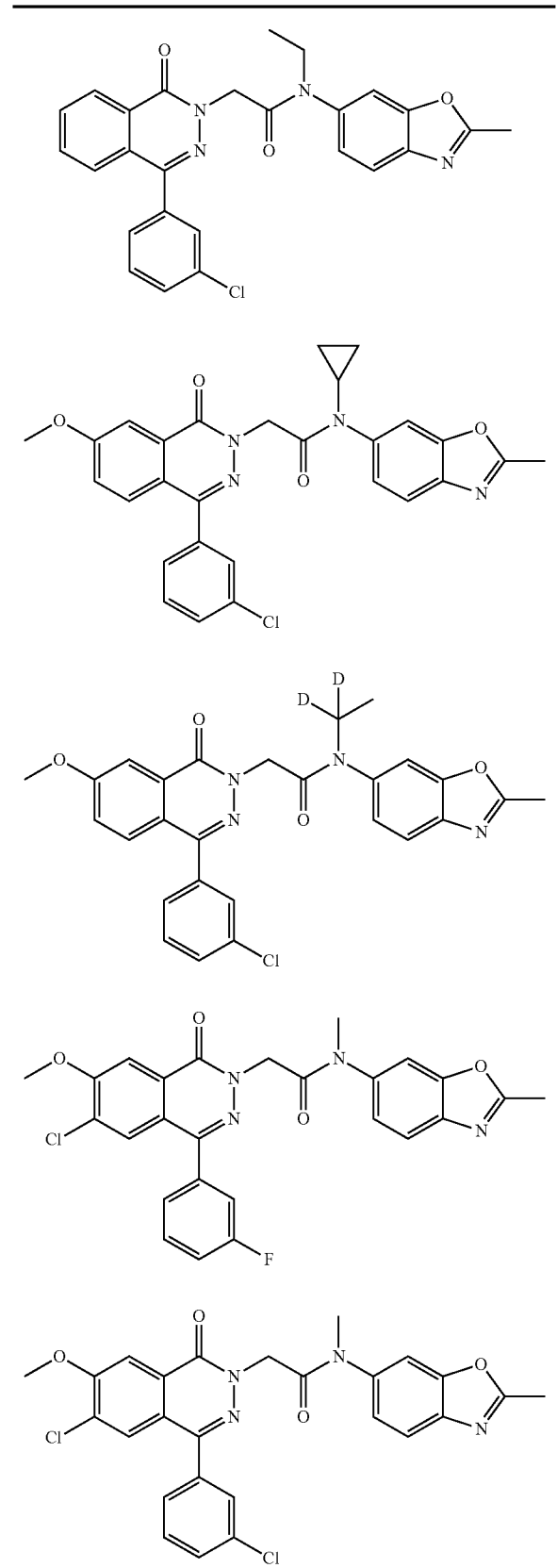
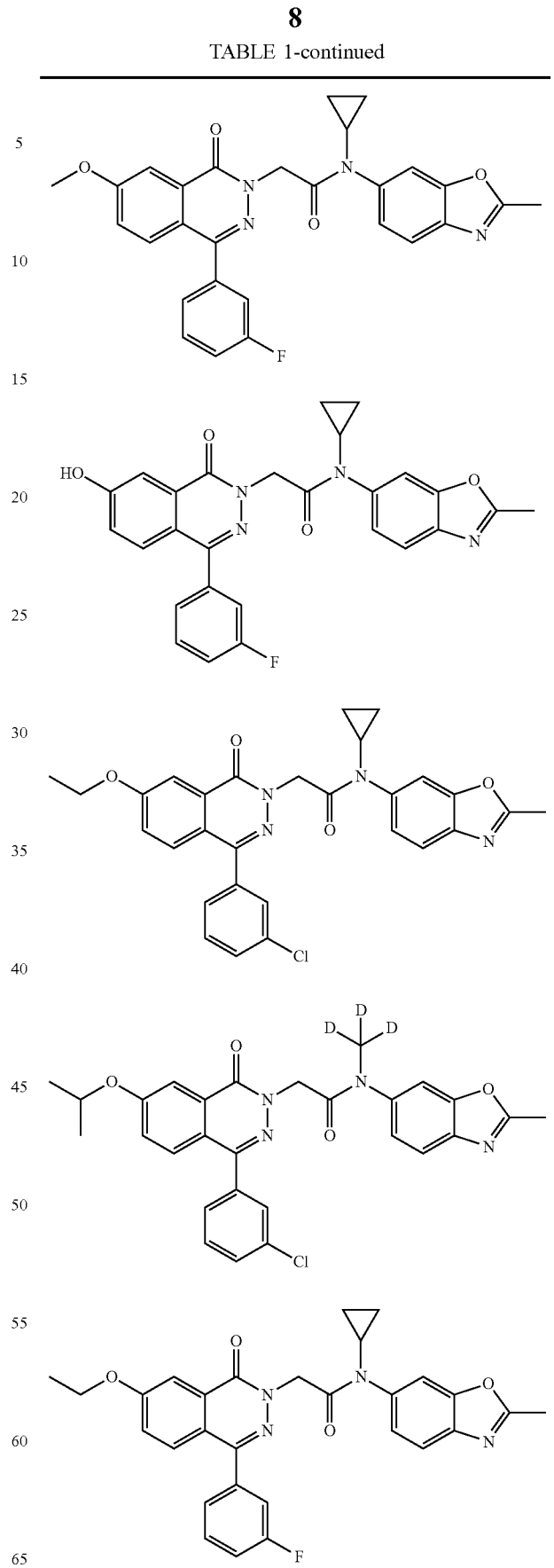

TABLE 1-continued
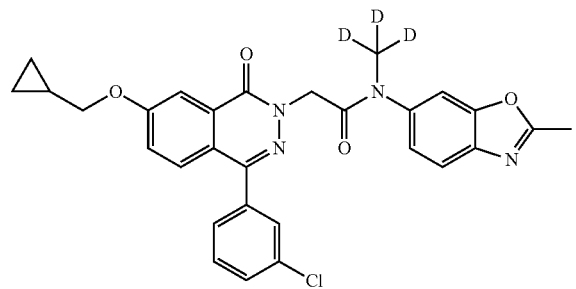 [SMILES: [2H]C([2H])([2H])N(C(=O)Cn1nc(-c2cccc(Cl)c2)c2ccc(OCC3CC3)cc2c1=O)c1ccc2nc(C)oc2c1]
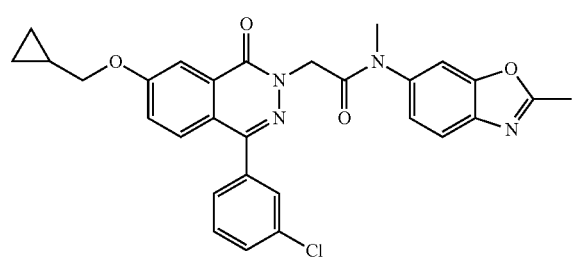 [SMILES: Cc1nc2ccc(N(C)C(=O)Cn3nc(-c4cccc(Cl)c4)c4ccc(OCC5CC5)cc4c3=O)cc2o1]
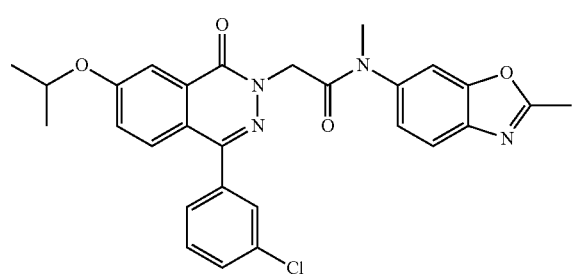 [SMILES: Cc1nc2ccc(N(C)C(=O)Cn3nc(-c4cccc(Cl)c4)c4ccc(OC(C)C)cc4c3=O)cc2o1]
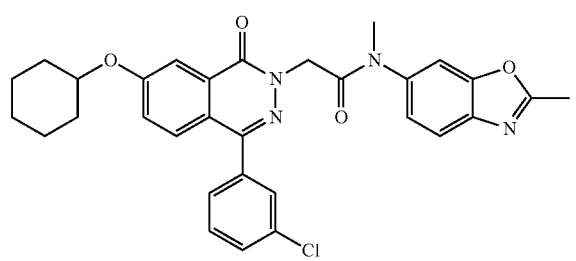 [SMILES: Cc1nc2ccc(N(C)C(=O)Cn3nc(-c4cccc(Cl)c4)c4ccc(OC5CCCCC5)cc4c3=O)cc2o1]
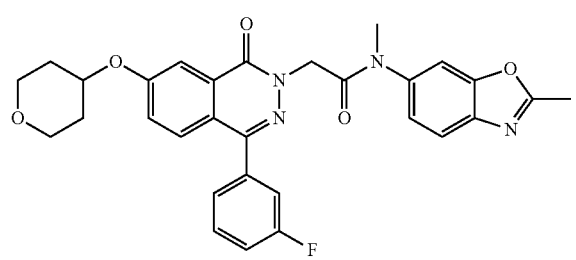 [SMILES: Cc1nc2ccc(N(C)C(=O)Cn3nc(-c4cccc(F)c4)c4ccc(OC5CCOCC5)cc4c3=O)cc2o1]
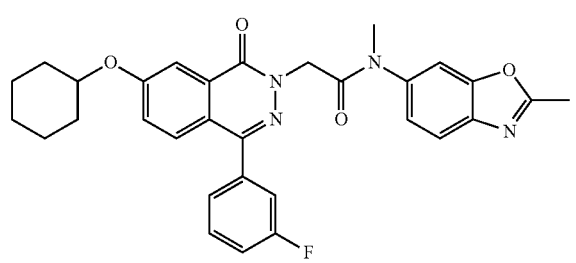
TABLE 1-continued
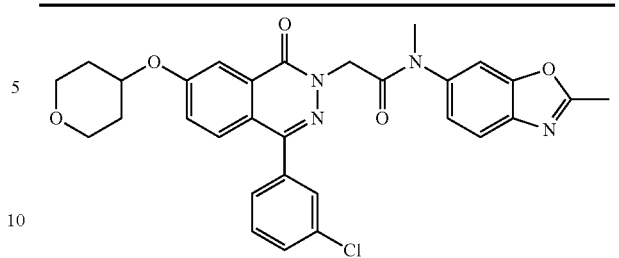
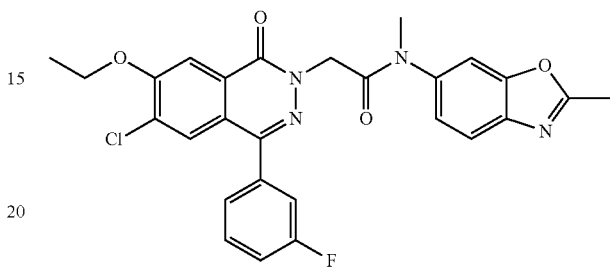
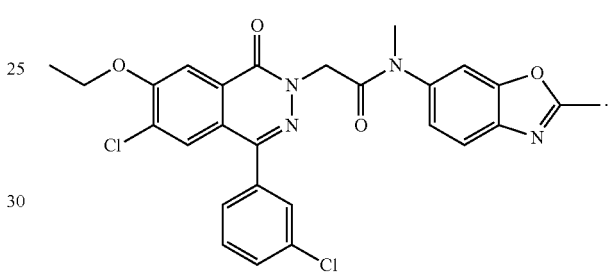
In a preferred embodiment, the invention relates to a compound of formula:
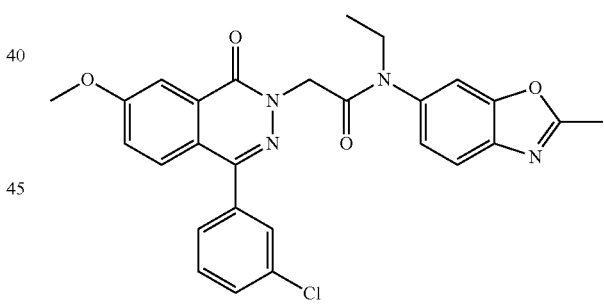
or a pharmaceutically acceptable salt thereof.
In a preferred embodiment, the invention relates to a compound of formula:
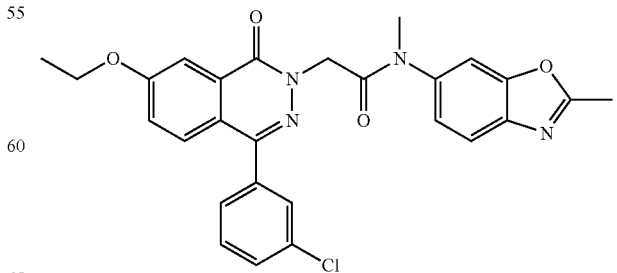
or a pharmaceutically acceptable salt thereof.

In a preferred embodiment, the invention relates to a compound of formula:

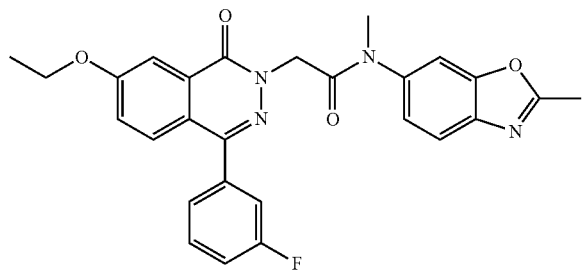 [SMILES: CCOc1ccc2c(-c3cccc(F)c3)nn(CC(=O)N(C)c3ccc4nc(C)oc4c3)c(=O)c2c1]

or a pharmaceutically acceptable salt thereof.

In a preferred embodiment, the invention relates to a compound of formula:

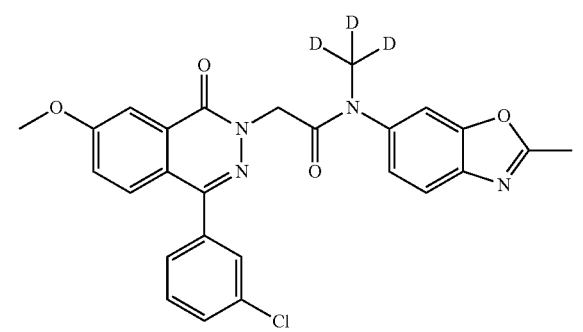

or a pharmaceutically acceptable salt thereof.

In a preferred embodiment, the invention relates to a compound of formula:

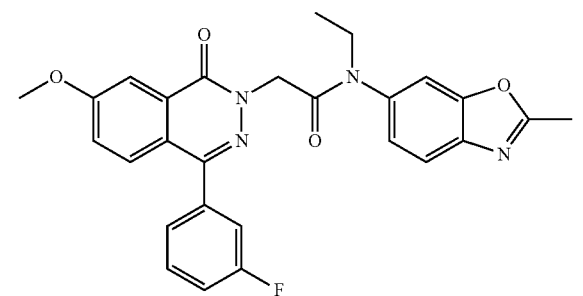

or a pharmaceutically acceptable salt thereof.

In a preferred embodiment, the invention relates to a compound of formula:

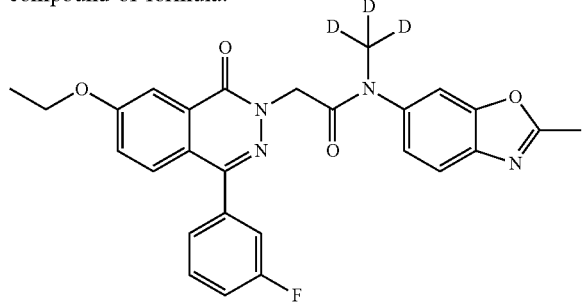 [SMILES: [2H]C([2H])([2H])N(C(=O)Cn1nc(-c2cccc(F)c2)c2ccc(OCC)cc2c1=O)c1ccc2nc(C)oc2c1]

or a pharmaceutically acceptable salt thereof.

In a preferred embodiment, the invention relates to a compound of formula:

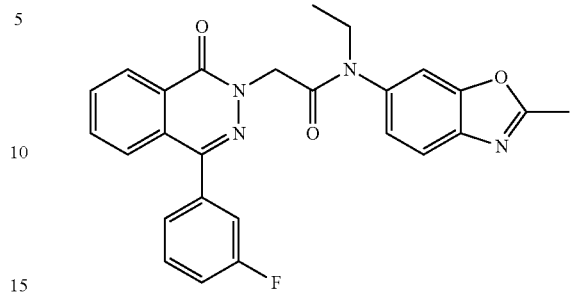

or a pharmaceutically acceptable salt thereof.

In a preferred embodiment, the invention relates to a compound of formula:

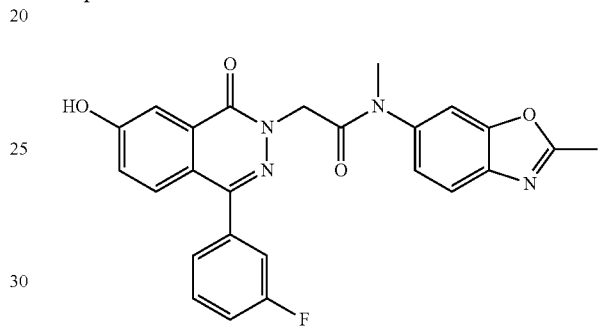

or a pharmaceutically acceptable salt thereof.

In a preferred embodiment, the invention relates to a compound of formula:

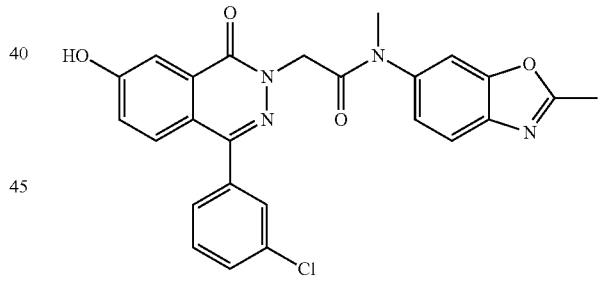

or a pharmaceutically acceptable salt thereof.

In a preferred embodiment, the invention relates to a compound of formula:

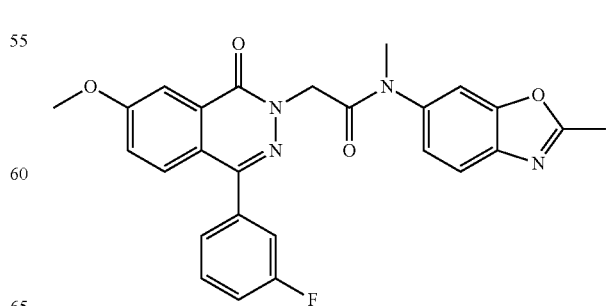

or a pharmaceutically acceptable salt thereof.

In a preferred embodiment, the invention relates to a compound of formula:

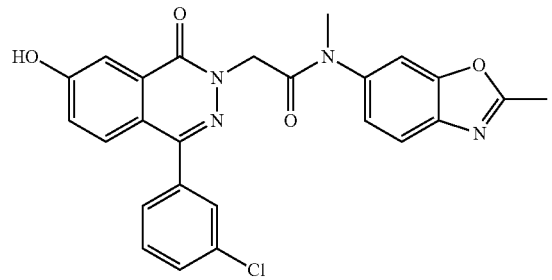

or a pharmaceutically acceptable salt thereof.

In a preferred embodiment, the invention relates to a compound of formula:

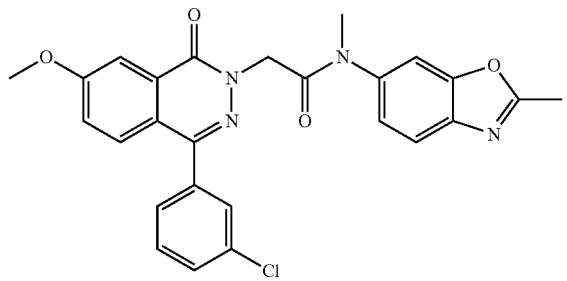

or a pharmaceutically acceptable salt thereof.

In a preferred embodiment, the invention relates to a compound of formula:

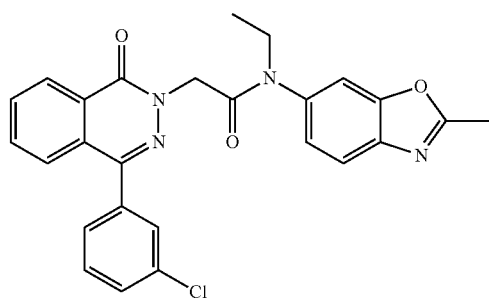 [SMILES: CCN(C(=O)Cn1nc(-c2cccc(Cl)c2)c2ccccc2c1=O)c1ccc2nc(C)oc2c1]

or a pharmaceutically acceptable salt thereof.

The compounds of this invention may be prepared by methods known in the art. Exemplary synthetic routes to prepare compounds of this invention are illustrated below:

Scheme 1

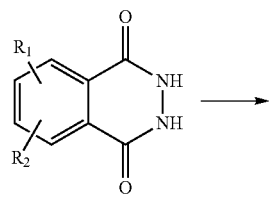

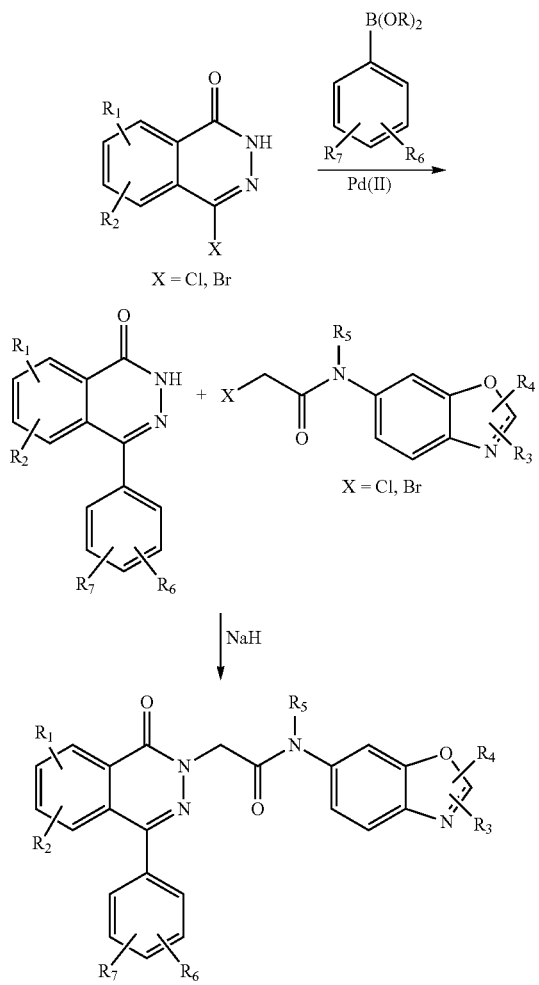

Scheme 2

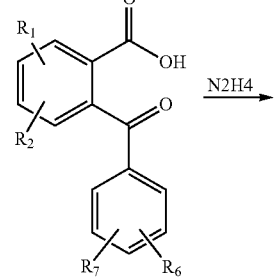

-continued

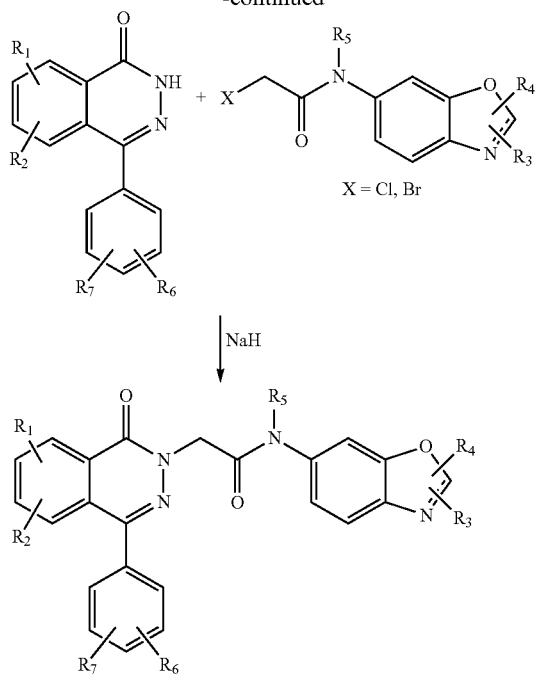

Scheme 3

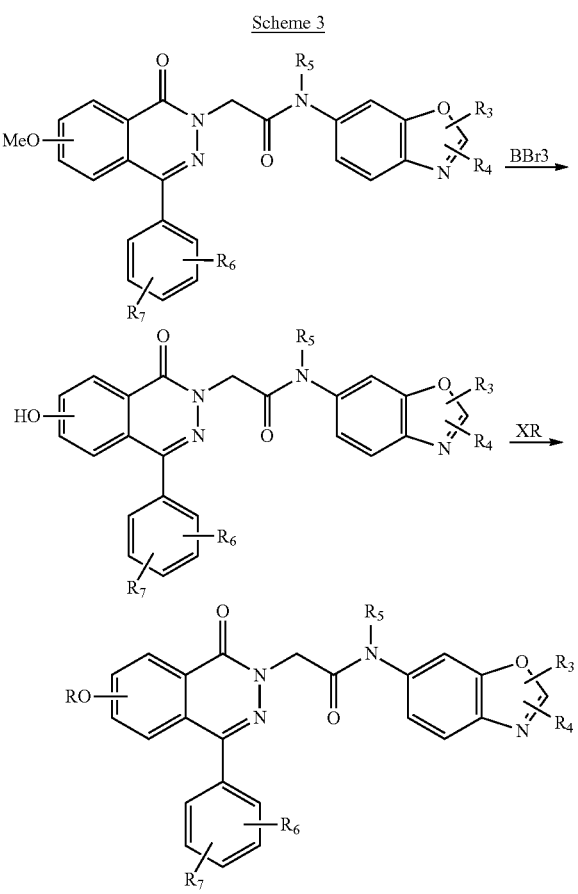

Compounds of the invention are useful as modulators of CFTR and treating diseases or disorders mediated by CFTR such as for the treatment of disease, disorders or conditions such as cystic fibrosis, hereditary emphysema, hereditary hemochromatosis, coagulation-fibrinolysis deficiencies, type 1 hereditary angioedema, lipid processing deficiencies, such as familial hypercholesterolemia, type 1 chylomicronemia, abetalipoproteinemia, lysosomal storage diseases, such as I-cell disease/pseudo Hurler, mucopolysaccharidoses, Sandhof/Tay-Sachs, Crigler-Najjar type 11, polyendocrinopathy/hyperinsulemia, diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, diabetes insipidus (DI), neurophyseal DI, neprogenic DI, Charcot-Marie tooth syndrome, Perlizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders disorders such as Huntington's disease, Spinocerebullar ataxia type I, Spinal and bulbar muscular atrophy, Dentororubal pallidoluysian, and Myotic dystrophy, as well as, spongiform encephalopathies such as Hereditary Creutzfeldt-Jakob disease, Fabry disease, Straussler-Scheinker disease, secretory diarrhea, polycystic kidney disease, chronic obstructive pulmonary disease (COPD), dry eye disease, or Sjogren's Syndrome.

The compounds of the invention may be administered in combination with antibiotics, anti-inflammatory medicines, bronchodilators, or mucus-thinning medicines. In particular antibiotics for the treatment of bacteria mucoid *Pseudomonas* may be used in combination with compounds of the invention. Inhaled antibiotics such as tobramycin, colistin, and aztreonam can be used in combination with treatment with compounds of the invention. Anti-inflammatory medicines may also be used in combination with compounds of the invention to treat CFTR related diseases. Bronchodilators can be used in combination with compounds of the invention to treat CFTR related diseases.

In one embodiment, the invention relates to combination therapy comprising compounds of the invention and other pharmaceutical agents useful for the treatment of CF. In a preferred embodiment, the aminoglycoside gentamicin can be used. In a preferred embodiment, ataluren, Ivacaftor (Kalydeco) or VX-809 may be used in combination with compounds of the invention.

In one embodiment, the invention relates to the administration of a compound of Formula I or a compound of Table 1 to a subject undergoing treatment with an aminoglycoside, ataluren, Ivacaftor or VX-809.

In one embodiment, the invention relates to pharmaceutical compositions comprising compounds of the invention and pharmaceutically acceptable carriers. The compositions may include compounds of the invention, and optionally a pharmaceutically acceptable carrier, adjuvant or vehicle. In certain embodiments, these compositions optionally further comprise one or more additional therapeutic agents useful for the treatment of CFTR mediated diseases or disorders.

Pharmaceutical Compositions

The pharmaceutical compositions of the present invention comprise a therapeutically effective amount of a compound of the present invention formulated together with one or more pharmaceutically acceptable carriers or excipients.

As used herein, the term "pharmaceutically acceptable carrier or excipient" means a non-toxic, inert solid, semi-solid, gel or liquid filler, diluent, encapsulating material or formulation auxiliary of any type. Some examples of materials which can serve as pharmaceutically acceptable carriers are sugars such as lactose, glucose and sucrose; cyclodextrins such as alpha-(α), beta-(β) and gamma-(γ) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir. In a preferred embodiment, administration is parenteral administration by injection.

The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, EtOAc, benzyl alcohol, benzyl benzoate, propylene glycol, 1, 3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable suspension or emulsion, such as INTRALIPID®, LIPOSYN® or OMEGAVEN®, or solution, in a nontoxic parenterally acceptable diluent or solvent, for example, as a solution in 1, 3-butanediol. INTRALIPID® is an intravenous fat emulsion containing 10-30% soybean oil, 1-10% egg yolk phospholipids, 1-10% glycerin and water. LIPOSYN® is also an intravenous fat emulsion containing 2-15% safflower oil, 2-15% soybean oil, 0.5-5% egg phosphatides 1-10% glycerin and water. OMEGAVEN® is an emulsion for infusion containing about 5-25% fish oil, 0.5-10% egg phosphatides, 1-10% glycerin and water. Among the acceptable vehicles and solvents that may be employed are water, Ringer's solution, USP and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration e.g., inhalation into the respiratory system. Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics is known in the art (see, for example U.S. Pat. No. 5,767,068 to VanDevanter et al., U.S. Pat. No. 5,508,269 to Smith et al., and WO 98/43650 by Montgomery).

Definitions

Listed below are definitions of various terms used to describe this invention. These definitions apply to the terms as they are used throughout this specification and claims, unless otherwise limited in specific instances, either individually or as part of a larger group.

The term "aliphatic group" or "aliphatic" refers to a non-aromatic moiety that may be saturated (e.g. single bond) or contain one or more units of unsaturation, e.g., double and/or triple bonds. An aliphatic group may be straight chained, branched or cyclic, contain carbon, hydrogen or, optionally, one or more heteroatoms and may be substituted or unsubstituted. In addition to aliphatic hydrocarbon groups, aliphatic groups include, for example, polyalkoxyalkyls, such as polyalkylene glycols, polyamines, and polyimines, for example. Such aliphatic groups may be further substituted. It is understood that aliphatic groups may include alkyl, substituted alkyl, alkenyl, substituted alkenyl, alkynyl, substituted alkynyl, and substituted or unsubstituted cycloalkyl groups as described herein.

The term "acyl" refers to a carbonyl substituted with hydrogen, alkyl, partially saturated or fully saturated cycloalkyl, partially saturated or fully saturated heterocycle, aryl, or heteroaryl. For example, acyl includes groups such as ($C_1$-$C_6$) alkanoyl (e.g., formyl, acetyl, propionyl, butyryl, valeryl, caproyl, t-butylacetyl, etc.), ($C_3$-$C_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" is intended to include both branched and straight chain, substituted or unsubstituted saturated aliphatic hydrocarbon radicals/groups having the specified number of carbons. Preferred alkyl groups comprise about 1 to about 24 carbon atoms ("$C_1$-$C_{24}$"). Other preferred alkyl groups comprise at about 1 to about 8 carbon atoms ("$C_1$-$C_8$") such as about 1 to about 6 carbon atoms ("$C_1$-$C_6$"), or such as about 1 to about 3 carbon atoms ("$C_1$-$C_3$"). Examples of $C_1$-$C_6$ alkyl radicals include, but are not limited to, methyl, ethyl, propyl, isopropyl, n-butyl, tert-butyl, n-pentyl, neopentyl and n-hexyl radicals.

The term "alkenyl" refers to linear or branched radicals having at least one carbon-carbon double bond. Such radicals preferably contain from about two to about twenty-four carbon atoms ("$C_2$-$C_{24}$"). Other preferred alkenyl radicals are "lower alkenyl" radicals having two to about ten carbon atoms ("$C_2$-$C_{10}$") such as ethenyl, allyl, propenyl, butenyl and 4-methylbutenyl. Preferred lower alkenyl radicals include 2 to about 6 carbon atoms ("$C_2$-$C_6$"). The terms "alkenyl", and "lower alkenyl", embrace radicals having "cis" and "trans" orientations, or alternatively, "E" and "Z" orientations.

The term "alkynyl" refers to linear or branched radicals having at least one carbon-carbon triple bond. Such radicals preferably contain from about two to about twenty-four carbon atoms ("$C_2$-$C_{24}$"). Other preferred alkynyl radicals are "lower alkynyl" radicals having two to about ten carbon atoms such as propargyl, 1-propynyl, 2-propynyl, 1-butyne, 2-butynyl and 1-pentynyl. Preferred lower alkynyl radicals include 2 to about 6 carbon atoms ("$C_2$-$C_6$").

The term "cycloalkyl" refers to saturated carbocyclic radicals having three to about twelve carbon atoms ("$C_3$-$C_{12}$"). The term "cycloalkyl" embraces saturated carbocyclic radicals having three to about twelve carbon atoms. Examples of such radicals include cyclopropyl, cyclobutyl, cyclopentyl and cyclohexyl.

The term "cycloalkenyl" refers to partially unsaturated carbocyclic radicals having three to twelve carbon atoms. Cycloalkenyl radicals that are partially unsaturated carbocyclic radicals that contain two double bonds (that may or may not be conjugated) can be called "cycloalkyldienyl". More preferred cycloalkenyl radicals are "lower cycloalkenyl" radicals having four to about eight carbon atoms. Examples of such radicals include cyclobutenyl, cyclopentenyl and cyclohexenyl.

The term "alkylene," as used herein, refers to a divalent group derived from a straight chain or branched saturated hydrocarbon chain having the specified number of carbons atoms. Examples of alkylene groups include, but are not limited to, ethylene, propylene, butylene, 3-methyl-pentylene, and 5-ethyl-hexylene.

The term "alkenylene," as used herein, denotes a divalent group derived from a straight chain or branched hydrocarbon moiety containing the specified number of carbon atoms having at least one carbon-carbon double bond. Alkenylene groups include, but are not limited to, for example, ethenylene, 2-propenylene, 2-butenylene, 1-methyl-2-buten-1-ylene, and the like.

The term "alkynylene," as used herein, denotes a divalent group derived from a straight chain or branched hydrocarbon moiety containing the specified number of carbon atoms having at least one carbon-carbon triple bond. Representative alkynylene groups include, but are not limited to, for example, propynylene, 1-butynylene, 2-methyl-3-hexynylene, and the like.

The term "alkoxy" refers to linear or branched oxy-containing radicals each having alkyl portions of one to about twenty-four carbon atoms or, preferably, one to about twelve carbon atoms. More preferred alkoxy radicals are "lower alkoxy" radicals having one to about ten carbon atoms and more preferably having one to about eight carbon atoms. Examples of such radicals include methoxy, ethoxy, propoxy, butoxy and tert-butoxy.

The term "alkoxyalkyl" refers to alkyl radicals having one or more alkoxy radicals attached to the alkyl radical, that is, to form monoalkoxyalkyl and dialkoxyalkyl radicals.

The term "aryl", alone or in combination, means an aromatic system containing one, two or three rings wherein such rings may be attached together in a pendent manner or may be fused. The term "aryl" embraces aromatic radicals such as phenyl, naphthyl, tetrahydronaphthyl, indane furanyl, quinazolinyl, pyridyl and biphenyl.

The terms "heterocyclyl", "heterocycle" "heterocyclic" or "heterocyclo" refer to saturated, partially unsaturated and unsaturated heteroatom-containing ring-shaped radicals, which can also be called "heterocyclyl", "heterocycloalkenyl" and "heteroaryl" correspondingly, where the heteroatoms may be selected from nitrogen, sulfur and oxygen. Examples of saturated heterocyclyl radicals include saturated 3 to 6-membered heteromonocyclic group containing 1 to 4 nitrogen atoms (e.g. pyrrolidinyl, imidazolidinyl, piperidino, piperazinyl, etc.); saturated 3 to 6-membered heteromonocyclic group containing 1 to 2 oxygen atoms and 1 to 3 nitrogen atoms (e.g. morpholinyl, etc.); saturated 3 to 6-membered heteromonocyclic group containing 1 to 2 sulfur atoms and 1 to 3 nitrogen atoms (e.g., thiazolidinyl, etc.). Examples of partially unsaturated heterocyclyl radicals include dihydrothiophene, dihydropyran, dihydrofuran and dihydrothiazole. Heterocyclyl radicals may include a pentavalent nitrogen, such as in tetrazolium and pyridinium radicals. The term "heterocycle" also embraces radicals where heterocyclyl radicals are fused with aryl or cycloalkyl radicals. Examples of such fused bicyclic radicals include benzofuran, benzothiophene, and the like.

The term "heteroaryl" refers to unsaturated aromatic heterocyclyl radicals. Examples of heteroaryl radicals include unsaturated 3 to 6 membered heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1, 2, 4-triazolyl, 1H-1, 2, 3-triazolyl, 2H-1, 2, 3-triazolyl, etc.) tetrazolyl (e.g. 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1, 5-b]pyridazinyl, etc.), etc.; unsaturated 3 to 6-membered heteromonocyclic group containing an oxygen atom, for example, pyranyl, furyl, etc.; unsaturated 3 to 6-membered heteromonocyclic group containing a sulfur atom, for example, thienyl, etc.; unsaturated 3- to 6-membered heteromonocyclic group containing 1 to 2 oxygen atoms and 1 to 3 nitrogen atoms, for example, oxazolyl, isoxazolyl, oxadiazolyl (e.g., 1, 2, 4-oxadiazolyl, 1, 3, 4-oxadiazolyl, 1, 2, 5-oxadiazolyl, etc.) etc.; unsaturated condensed heterocyclyl group containing 1 to 2 oxygen atoms and 1 to 3 nitrogen atoms (e.g. benzoxazolyl, benzoxadiazolyl, etc.); unsaturated 3 to 6-membered heteromonocyclic group containing 1 to 2 sulfur atoms and 1 to 3 nitrogen atoms, for example, thiazolyl, thiadiazolyl (e.g., 1, 2, 4-thiadiazolyl, 1, 3, 4-thiadiazolyl, 1, 2, 5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "heterocycloalkyl" refers to heterocyclo-substituted alkyl radicals. More preferred heterocycloalkyl radicals are "lower heterocycloalkyl" radicals having one to six carbon atoms in the heterocyclo radical.

The term "alkylthio" refers to radicals containing a linear or branched alkyl radical, of one to about ten carbon atoms attached to a divalent sulfur atom. Preferred alkylthio radicals have alkyl radicals of one to about twenty-four carbon atoms or, preferably, one to about twelve carbon atoms. More preferred alkylthio radicals have alkyl radicals which are "lower alkylthio" radicals having one to about ten carbon atoms. Most preferred are alkylthio radicals having lower alkyl radicals of one to about eight carbon atoms. Examples of such lower alkylthio radicals include methylthio, ethylthio, propylthio, butylthio and hexylthio.

The terms "aralkyl" or "arylalkyl" refer to aryl-substituted alkyl radicals such as benzyl, diphenylmethyl, triphenylmethyl, phenylethyl, and diphenylethyl.

The term "aryloxy" refers to aryl radicals attached through an oxygen atom to other radicals.

The terms "aralkoxy" or "arylalkoxy" refer to aralkyl radicals attached through an oxygen atom to other radicals.

The term "aminoalkyl" refers to alkyl radicals substituted with amino radicals. Preferred aminoalkyl radicals have alkyl radicals having about one to about twenty-four carbon atoms or, preferably, one to about twelve carbon atoms. More preferred aminoalkyl radicals are "lower aminoalkyl" that have alkyl radicals having one to about ten carbon atoms. Most preferred are aminoalkyl radicals having lower alkyl radicals having one to eight carbon atoms. Examples of such radicals include aminomethyl, aminoethyl, and the like.

The term "alkylamino" denotes amino groups which are substituted with one or two alkyl radicals. Preferred alkylamino radicals have alkyl radicals having about one to about twenty carbon atoms or, preferably, one to about twelve carbon atoms. More preferred alkylamino radicals are "lower alkylamino" that have alkyl radicals having one to about ten carbon atoms. Most preferred are alkylamino radicals having lower alkyl radicals having one to about eight carbon atoms. Suitable lower alkylamino may be monosubstituted N-alkylamino or disubstituted N, N-alkylamino, such as N-methylamino, N-ethylamino, N, N-dimethylamino, N, N-diethylamino or the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkyl sulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

For simplicity, chemical moieties that are defined and referred to throughout can be univalent chemical moieties (e.g., alkyl, aryl, etc.) or multivalent moieties under the appropriate structural circumstances clear to those skilled in the art. For example, an "alkyl" moiety can be referred to a monovalent radical (e.g. $CH_3$—$CH_2$—), or in other instances, a bivalent linking moiety can be "alkyl," in which case those skilled in the art will understand the alkyl to be a divalent radical (e.g., —$CH_2$—$CH_2$—), which is equivalent to the term "alkylene." Similarly, in circumstances in which divalent moieties are required and are stated as being "alkoxy", "alkylamino", "aryloxy", "alkylthio", "aryl", "heteroaryl", "heterocyclic", "alkyl" "alkenyl", "alkynyl", "aliphatic", or "cycloalkyl", those skilled in the art will understand that the terms "alkoxy", "alkylamino", "aryloxy", "alkylthio", "aryl", "heteroaryl", "heterocyclic", "alkyl", "alkenyl", "alkynyl", "aliphatic", or "cycloalkyl" refer to the corresponding divalent moiety.

The terms "halogen" or "halo" as used herein, refers to an atom selected from fluorine, chlorine, bromine and iodine.

The terms "compound" "drug," and "prodrug" as used herein all include pharmaceutically acceptable salts, co-crystals, solvates, hydrates, polymorphs, enantiomers, diastereoisomers, racemates and the like of the compounds, drugs and prodrugs having the formulas as set forth herein.

Substituents indicated as attached through variable points of attachments can be attached to any available position on the ring structure.

As used herein, the term "effective amount of the subject compounds," with respect to the subject method of treatment, refers to an amount of the subject compound which, when delivered as part of desired dose regimen, brings about management of the disease or disorder to clinically acceptable standards.

"Treatment" or "treating" refers to an approach for obtaining beneficial or desired clinical results in a patient. For purposes of this invention, beneficial or desired clinical results include, but are not limited to, one or more of the following: alleviation of symptoms, diminishment of extent of a disease, stabilization (i.e., not worsening) of a state of disease, preventing spread (i.e., metastasis) of disease, preventing occurrence or recurrence of disease, delay or slowing of disease progression, amelioration of the disease state, and remission (whether partial or total).

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

4-(3-chlorophenyl)phthalazin-1(2H)-one

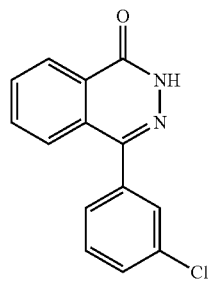 [SMILES: O=c1[nH]nc(-c2cccc(Cl)c2)c2ccccc12]

A solution of 1-chlorophthalazine-4-one (1.0 g, 5.5 mmol), 3-chlorophenyl boronic acid (1.3 g, 8.3 mmol), tricyclohexyphosphine (0.058 g, 0.27 mmol), and $K_3PO_4$ (2.3 g, 11.0 mmol) in THF (20 mL) and water (5 mL) was degassed with $N_2$ for 30 min then treated with tri(dibenzylideneacetone)-dipalladium (0.050 g, 0.05 mmol) and heated at reflux overnight. The reaction mixture was diluted with water (100 mL) and the product extracted with EtOAc (2×100 mL). The organics were washed with brine, dried over $Na_2SO_4$, and concentrated to give 4-(3-chlorophenyl)phthalazin-1(2H)-one (1.2 g), (MS: ESI+ve, 257.12 [M+H]). $^1$H NMR: (400 MHz, DMSO) δ: 7.58-7.60 (m, 2H), 7.61-7.64 (m, 2H), 7.65-7.67 (m, 1H), 7.90-7.93 (m, 2H), 8.34-8.36 (m, 1H). 12.93 (s, 1H).

Example 1: 2-(4-(3-chlorophenyl)-1-oxophthalazin-2(1H)-yl)-N-methyl-N-(2-methylbenzo[d]oxazol-6-yl)acetamide

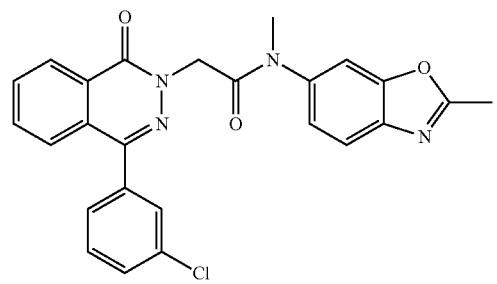

To a solution of 4-(3-chlorophenyl)phthalazin-1(2H)-one (0.5 g, 1.94 mmol) in DMF (20 mL) was added NaH (60%) (0.116 g, 2.91 mmol) portionwise at 0° C. After stirring for 30 min, 2-bromo-N-methyl-N-(2-methylbenzo[d]oxazol-6-yl) acetamide (0.55 g, 1.94 mmol) in DMF (2 mL) was added dropwise and the reaction mixture warmed to rt overnight. The reaction was quenched with water and the solid collected by filtration. The crude was purified by column chromatography (60-70% EtOAc/hexane) to give 2-(4-(3-chlorophenyl)-1-oxophthalazin-2(1H)-yl)-N-methyl-N-(2-methylbenzo[d]oxazol-6-yl)acetamide (0.22 g), (MS: ESI+ve, 459.17 [M+H]). $^1$H NMR: (400 MHz, DMSO) δ: 2.63 (s, 3H), 3.24 (s, 3H), 4.73 (s, 2H), 7.44-7.46 (d, J=8.0, 1H), 7.55-7.66 (m, 4H), 7.69-7.74 (q, 2H), 7.93 (s, 3H), 8.29-8.31 (d, J=7.2, 1H). Representative compounds of the invention were prepared in a similar manner to examples 1 from 4-chlorophthalazin-1(2H)-one, the corresponding boronic acid or ester, and the appropriate alkylating agent (scheme 1).

| 2. | 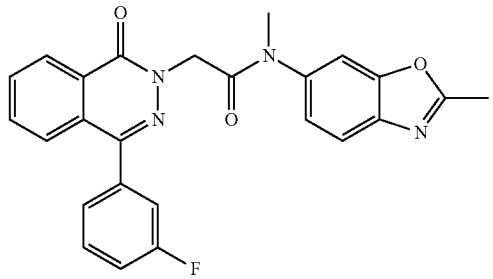 [SMILES: Cc1nc2ccc(N(C)C(=O)Cn3nc(-c4cccc(F)c4)c4ccccc4c3=O)cc2o1] | 2-(4-(3-fluorophenyl)-1-oxophthalazin-2(1H)-yl)-N-methyl-N-(2-methylbenzo[d]oxazol-6-yl)acetamide | 443 [M + H] |

2-methylbenzo[d]oxazol-6-amine

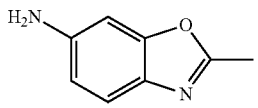

2-Methyl-6-nitrobenzoxazole (10.0 g, 56 mmol) and 10% Pd/C (3.4 g) in MeOH (10 mL) were hydrogenated at rt for 16 h. The reaction mixture was filtered through Celite and wash with MeOH (100 mL). The filtrate was concentrated under vacuum to obtained crude 2-methylbenzo[d]oxazol-6-amine (8.4 g), (MS: ESI+ve, 149.07 [M+H]); $^1$H NMR: (400 MHz, DMSO) δ: 2.47 (s, 3H), 5.24 (s, 2H), 6.56-6.53 (dd, J=2, 1H), 6.70-6.70 (d, J=1.6, 1H), 7.25-7.23 (d, J=8.4, 1H).

2,2,2-trifluoro-N-(2-methylbenzo[d]oxazol-6-yl)acetamide

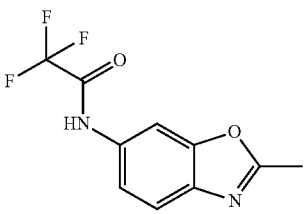 [SMILES: Cc1nc2ccc(NC(=O)C(F)(F)F)cc2o1]

A solution of 2-methylbenzo[d]oxazol-6-amine (8.4 g, 56.7 mmol) in pyridine (80 mL) at 0° C. was treated with TFAA (19.8 mL, 141.0 mmol) and stirred at rt for 4 h. The reaction mixture was diluted with water (100 mL) and the product extracted with EtOAc (3×100 mL). The organics were washed with brine, dried over Na$_2$SO$_4$, and concentrated to obtain the crude 2,2,2-trifluoro-N-(2-methylbenzo[d]oxazol-6-yl)acetamide (15.0 g), (MS: ESI+ve, 245.20 [M–H]); $^1$H NMR: (400 MHz, DMSO) δ: 2.61 (s, 3H), 7.61-7.56 (m, 1H), 7.69-7.67 (d, J=8.4, 1H), 8.04-8.04 (d, J=2, 1H), 11.45 (s, 1H).

2,2,2-trifluoro-N-methyl-N-(2-methylbenzo[d]oxazol-6-yl)acetamide

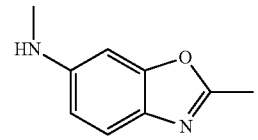

A solution of 2,2,2-trifluoro-N-(2-methylbenzo[d]oxazol-6-yl)acetamide (15.0 g, 61.2 mmol) in DMF (100 mL) was treated with K$_2$CO$_3$ (8.448 g, 61.2 mmol) and the reaction mixture was stirred at rt for 1 h, then cooled to 0° C. Iodomethane (3.9 mL, 64.2 mmol) was added dropwise and stirring continued at rt overnight. The reaction mixture was diluted with water (100 mL) and extracted with EtOAc (3×100 mL). The organics were washed with brine, dried over Na$_2$SO$_4$ and concentrated to obtain crude 2,2,2-trifluoro-N-methyl-N-(2-methylbenzo[d]oxazol-6-yl)acetamide (16.5 g), (MS: ESI+ve, 259.26 [M+H]).

N,2-dimethylbenzo[d]oxazol-6-amine

To a solution of crude 2,2,2-trifluoro-N-methyl-N-(2-methylbenzo[d]oxazol-6-yl)acetamide (16.5 g, 63.0 mmol) in MeOH (440 mL) and water (73 mL) was added K$_2$CO$_3$ (35.3 g, 25.5 mmol). The reaction mixture was stirred at reflux for 3 h, then concentrated under vacuum, diluted with water (50 mL), extracted with EtOAc (2×50 mL). The organics were washed with brine, dried over Na$_2$SO$_4$, and concentrated to obtain crude N,2-dimethylbenzo[d]oxazol-6-amine (8.3 g), (MS: ESI+ve, 163.12 [M+H]); $^1$H NMR: (400 MHz, DMSO) δ: 2.51 (s, 3H), 2.56 (s, 3H), 5.87-5.85 (m, 1H), 6.57-6.53 (m, 1H), 6.65-6.64 (d, J=2.4, 1H), 7.31-7.28 (t, 1H).

2-bromo-N-methyl-N-(2-methylbenzo[d]oxazol-6-yl)acetamide

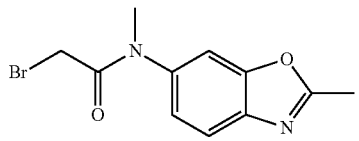 [SMILES: Cc1nc2ccc(N(C)C(=O)CBr)cc2o1]

To a solution of N,2-dimethylbenzo[d]oxazol-6-amine (9.4 g, 58.0 mmol) in DCM (100 mL) was added EDC.HCl (26.6 g, 139 mmol), DMAP (0.354 g, 2.9 mmol) and bromoacetic acid (18.5 g, 133.0 mmol) at 0° C. under $N_2$. The reaction mixture was stirred at rt overnight, then diluted with water (200 mL). The product was extracted with DCM (3×100 mL) and the organics were washed with brine, dried over $Na_2SO_4$ and concentrated to obtain 2-bromo-N-methyl-N-(2-methylbenzo[d]oxazol-6-yl)acetamide (10.0 g, 61%), (MS: ESI+ve, 283.1 [M+H]); $^1$H NMR: (400 MHz, DMSO) δ: 2.59 (s, 3H), 3.23 (s, 3H), 4.04 (s, 2H), 6.76-6.74 (d, J=8.8, 1H), 7.38-7.30 (dd, J=8.8, 1H), 7.73-7.71 (d, J=8, 1H).

3-fluoro-N-methoxy-N-methylbenzamide

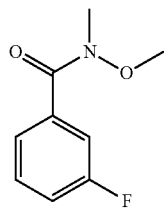

To a solution of 3-fluorobenzoic acid (30 g, 214.1 mmol) in DCM (300 mL) were added EDC.HCl (45 g, 235 mmol) and N,O-dimethylhydroxylamine.HCl (23 g, 235 mmol) at 0° C. under $N_2$. The reaction mixture was stirred at rt for 3 h, then diluted with water (1000 mL) and extracted with DCM (3×200 mL). The organics were washed with brine, dried over $Na_2SO_4$, and concentrated to obtain the 3-fluoro-N-methoxy-N-methylbenzamide (24 g, 61%). (183.91 [M+H]) 1H NMR: (400 MHz, $CDCl_3$) δ: 3.38 (s, 3H), 3.57 (s, 3H), 7.14-7.19 (m, 1H), 7.37-7.43 (m, 2H), 7.48-7.50 (d, J=7.6, 1H).

2-(3-fluorobenzoyl)-5-methoxybenzoic acid

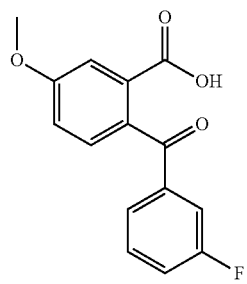 [SMILES: COc1ccc(C(=O)c2cccc(F)c2)c(C(=O)O)c1]

A −78° C. solution of 2-bromo-5-methoxybenzoic acid (26.0 g, 112.5 mmol) in THF (100 mL) was treated with n-BuLi (1.6 M in hexane) (140 mL, 225 mmol) and stirred at −78° C. for 1 h. 3-fluoro-N-methoxy-N-methylbenzamide (15.3 g, 83.8 mmol) in THF (40 mL) was added dropwise then warmed to rt for 16 h. The reaction mixture was diluted with water (100 mL), acidified with 5N HCl (25 mL) and extracted with EtOAc (3×200 mL). The organic layer was washed with brine, dried over $Na_2SO_4$, and concentrated to obtain 2-(3-fluorobenzoyl)-5-methoxybenzoic acid (21.0 g, 68%) (274.83 [M+H]); $^1$H NMR: (400 MHz, DMSO) δ: 3.89 (s, 3H), 7.26-7.29 (m, 1H), 7.37-7.45 (m, 4H), 7.50-7.55 (m, 2H).

4-(3-fluorophenyl)-7-methoxyphthalazin-1(2H)-one

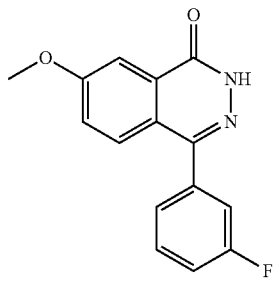 [SMILES: COc1ccc2c(-c3cccc(F)c3)n[nH]c(=O)c2c1]

A solution of 2-(3-fluorobenzoyl)-5-methoxybenzoic acid (21 g, 76.5 mmol) in hydrazine hydrate (4.09 mL, 84.0 mmol) and EtOH (300 mL) was heated overnight at 80° C. The reaction mixture was concentrated, diluted with water (300 mL), and the precipitate was filtered and dried to yield 4-(3-fluorophenyl)-7-methoxyphthalazin-1(2H)-one (7.2 g). (270.85 [M+H])$^1$H NMR: (400 MHz, DMSO) δ: 3.96 (s, 3H), 7.36-7.43 (m, 3H), 7.46-7.49 (m, 1H), 7.57-7.64 (m, 2H), 7.73-7.73 (d, J=2.8, 1H).

Example 3: 2-(4-(3-fluorophenyl)-7-methoxy-1-oxophthalazin-2(1H)-yl)-N-methyl-N-(2-methylbenzo[d]oxazol-6-yl)acetamide

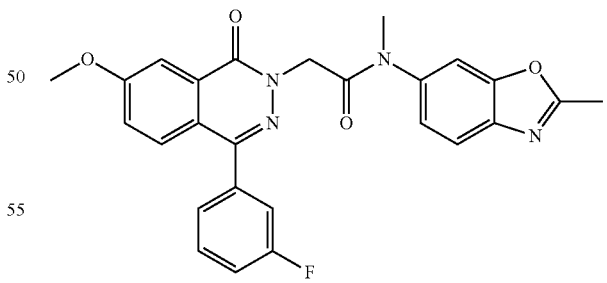

A 0° C. solution of 4-(3-fluorophenyl)-7-methoxyphthalazin-1(2H)-one (7.0 g, 25.9 mmol) in THF (160 mL) was treated with LiHMDS (1M in THF) (38 mL, 38 mmol) and stirred for 30 min. 2-Bromo-N-methyl-N-(2-methylbenzo[d]oxazol-6-yl)acetamide (7.33 g, 25.9 mmol) in THF (40 mL) was added dropwise and stirring was maintained at rt for 16 h. The reaction mixture was diluted with water (200 mL) and the product extracted with EtOAc (3×150 mL). The organics were washed with brine (100 mL), dried over Na$_2$SO$_4$, and concentrated. The crude was triturated with MeOH (250 mL) to yield 2-(4-(3-fluorophenyl)-7-methoxy-1-oxophthalazin-2(1H)-yl)-N-methyl-N-(2-methylbenzo[d]oxazol-6-yl)acetamide (9.1 g, 74%). (472.87 [M+H])$^1$H NMR: (400 MHz, DMSO) δ: 2.62 (s, 3H), 3.33 (s, 3H), 4.95 (s, 3H), 4.73 (s, 2H), 7.37-7.43 (m, 4H), 7.48-7.51 (d, J=2.4, 8.8, 1H), 7.58-7.73 (m, 4H), 7.90 (s, 1H).

Representative compounds of the invention were prepared in a similar manner to example 3 from the corresponding 2-bromobenzoic acid, N-methoxy-N-benzamide and appropriate alkylating agent (scheme 2).

| Example No. | Structure | IUPAC Name | LCMS m/z |
|---|---|---|---|
| 4. | 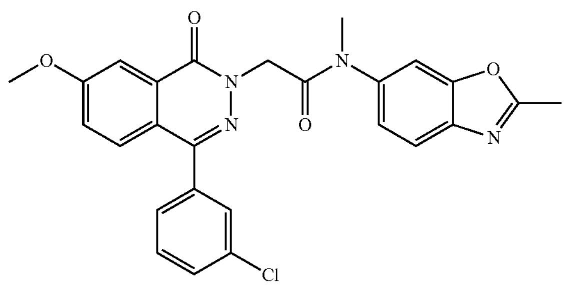 | 2-(4-(3-chlorophenyl)-7-methoxy-1-oxophthalazin-2(1H)-yl)-N-methyl-N-(2-methylbenzo[d]oxazol-6-yl)acetamide | 490 [M + H] |
| 5. | 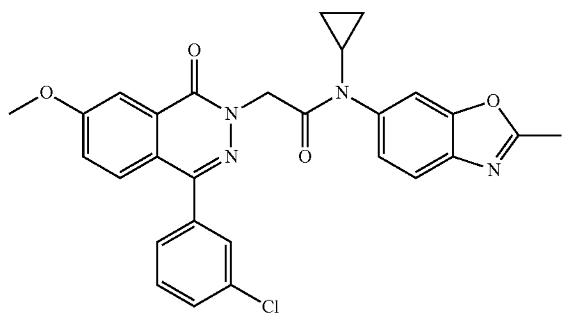 | 2-(4-(3-chlorophenyl)-7-methoxy-1-oxophthalazin-2(1H)-yl)-N-cyclopropyl-N-(2-methylbenzo[d]oxazol-6-yl)acetamide | 516 [M + H] |
| 6. | 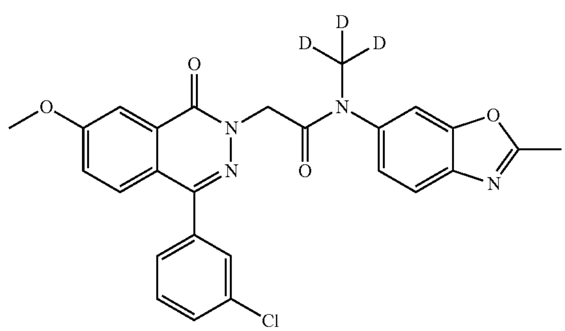 | 2-(4-(3-chlorophenyl)-7-methoxy-1-oxophthalazin-2(1H)-yl)-N-(methyl-d3)-N-(2-methylbenzo[d]oxazol-6-yl)acetamide | 493 [M + H] |
| 7. | 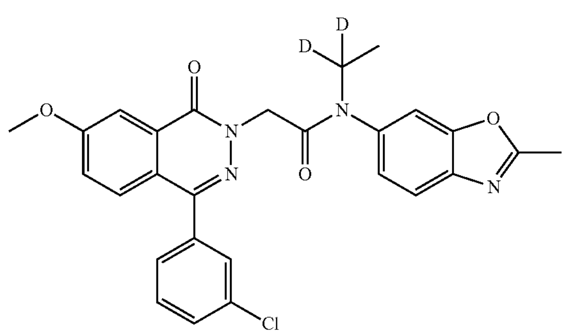 | 2-(4-(3-chlorophenyl)-7-methoxy-1-oxophthalazin-2(1H)-yl)-N-(ethyl-1,1-d2)-N-(2-methylbenzo[d]oxazol-6-yl)acetamide | 506 [M + H] |

-continued

| Example No. | Structure | IUPAC Name | LCMS m/z |
|---|---|---|---|
| 8. | 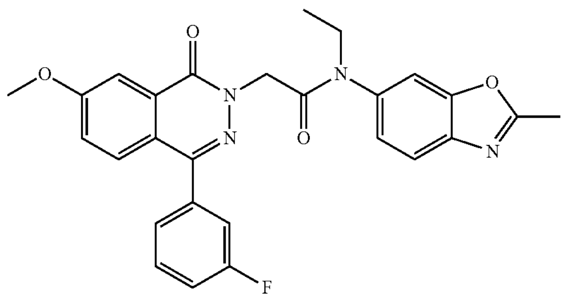 | N-ethyl-2-(4-(3-fluorophenyl)-7-methoxy-1-oxophthalazin-2(1H)-yl)-N-(2-methylbenzo[d]oxazol-6-yl)acetamide | 488 [M + H] |
| 9. | 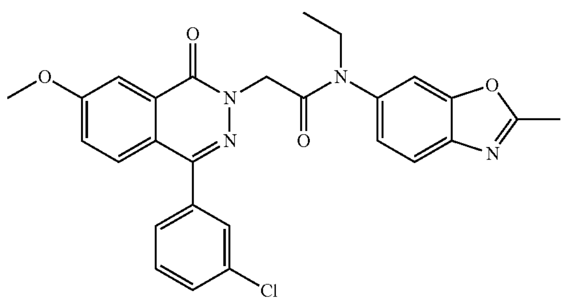 | 2-(4-(3-chlorophenyl)-7-methoxy-1-oxophthalazin-2(1H)-yl)-N-ethyl-N-(2-methylbenzo[d]oxazol-6-yl)acetamide | 504 [M + H] |
| 10. | 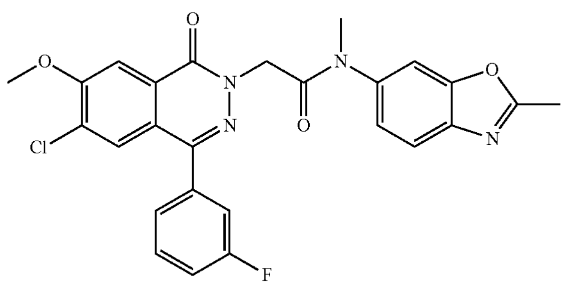 | 2-(6-chloro-4-(3-fluorophenyl)-7-methoxy-1-oxophthalazin-2(1H)-yl)-N-methyl-N-(2-methylbenzo[d]oxazol-6-yl)acetamide | 522 [M + H] |
| 11. | 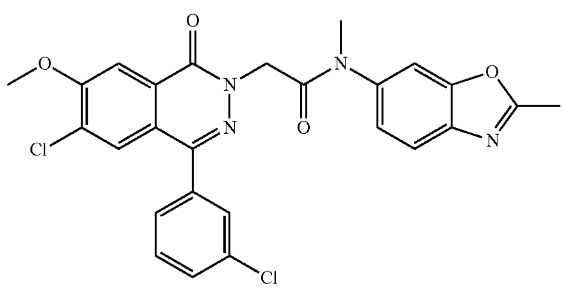 | 2-(6-chloro-4-(3-chlorophenyl)-7-methoxy-1-oxophthalazin-2(1H)-yl)-N-methyl-N-(2-methylbenzo[d]oxazol-6-yl)acetamide | 524 [M + H] |
| 12. | 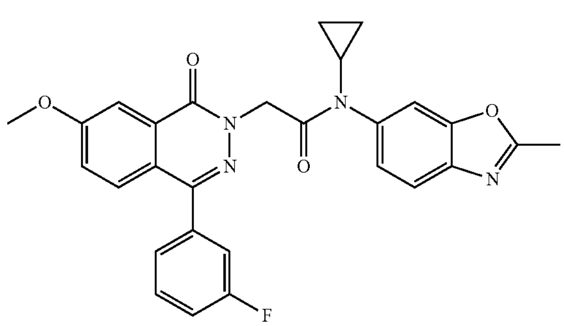 | N-cyclopropyl-2-(4-(3-fluorophenyl)-7-methoxy-1-oxophthalazin-2(1H)-yl)-N-(2-methylbenzo[d]oxazol-6-yl)acetamide | 500 [M + H] |

33

2-bromo-4-chloro-5-methoxybenzoic acid

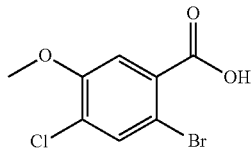

A solution of 4-chloro-3-methoxybenzoic acid (5.0 g, 26.7 mmol) in HOAc (25 mL) and water (25 mL) was treated slowly with Br₂ (1.6 mL 32 mmol). After heating to 60° C. for 2 h, the reaction was stirred cooled to rt overnight. It was quenched with water (300 mL), and the precipitate was filtered and dried to yield 2-bromo-4-chloro-5-methoxybenzoic acid (5.0 g, 70%). (264.87 [M−H])¹H NMR: (400 MHz, DMSO) δ: 3.90 (s, 3H), 7.46 (s, 1H), 7.82 (s, 1H), 13.63 (s, 1H).

4-chloro-2-(3-cyanobenzoyl)-5-methoxybenzoic acid

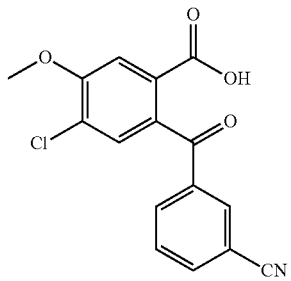 [SMILES: COc1cc(C(=O)O)c(C(=O)c2cccc(C#N)c2)cc1Cl]

A −78° C. solution of 2-bromo-4-chloro-5-methoxybenzoic acid (0.5 g, 1.88 mmol) in THF (15 mL) was treated with n-BuLi (1.6M in hexane) (1.7 ml, 2.82 mmol) and stirred for 1 h at −78° C. 3-Cyano-N-methoxy-N-methylbenzamide (0.35 g, 1.88 mmol) in THF (15 mL) was added dropwise and the reaction stirred for 1 h at −78° C., then overnight at rt. It was diluted with water (30 mL), acidified with 5N HCl (15 mL), and extracted with EtOAc (2×100 mL). The organic layer was washed with brine, dried over Na₂SO₄, and concentrated to obtain 4-chloro-2-(3-cyanobenzoyl)-5-methoxybenzoic acid (0.5 g, 84%) (316.33 [M−H]).

34

3-(7-chloro-6-methoxy-4-oxo-3,4-dihydrophthalazin-1-yl) benzonitrile

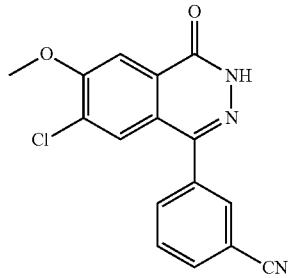 [SMILES: COc1cc2c(=O)[nH]nc(-c3cccc(C#N)c3)c2cc1Cl]

A solution of 4-chloro-2-(3-cyanobenzoyl)-5-methoxybenzoic acid (3.0 g, 9.50 mmol) in hydrazine hydrate (0.6 mL 11.4 mmol) and EtOH (40 mL) was heated at 80° C. for 2 h. The reaction mixture was diluted with water (100 mL), and the precipitate was filtered and dried to obtain 3-(7-chloro-6-methoxy-4-oxo-3,4-dihydrophthalazin-1-yl) benzonitrile (0.6 g, 17%) (312.4 [M+H])¹H NMR: (400 MHz, DMSO) δ: 3.96 (s, 3H), 7.64 (s, 1H), 7.79-7.75 (t, 1H), 7.87 (s, 1H), 7.96-7.94 (d, J=8, 1H), 8.04-8.02 (d, J=8, 1H), 8.09 (s, 1H), 13.03 (s, 1H).

Example 13: Synthesis of 2-(4-(3-fluorophenyl)-7-hydroxy-1-oxophthalazin-2(1H)-yl)-N-methyl-N-(2-methylbenzo[d]oxazol-6-yl)acetamide

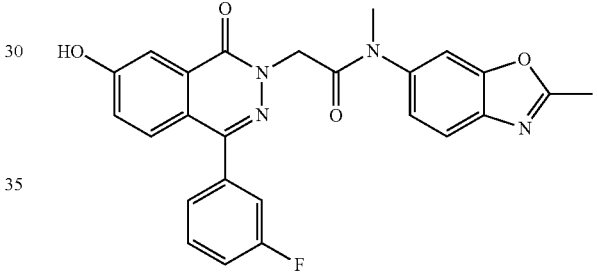

To a solution of 2-(4-(3-fluorophenyl)-7-methoxy-1-oxophthalazin-2(1H)-yl)-N-methyl-N-(2-methylbenzo[d]oxazol-6-yl)acetamide (example 70) (4.0 g, 8.469 mmol) in DCM (30 mL) was added BBr₃ (4.8 mL, 50.8 mmol) at 0° C. The reaction mixture was stirred at rt overnight then diluted with water (150 mL), neutralized with NaHCO₃, then extracted with DCM (3×100 mL). The organic layer was washed with brine (100 mL), dried over Na₂SO₄, and concentrated to yield 2-(4-(3-fluorophenyl)-7-hydroxy-1-oxophthalazin-2(1H)-yl)-N-methyl-N-(2-methylbenzo[d]oxazol-6-yl)acetamide (2.9 g, 74%) (459.36 [M+H]).

Representative compounds of the invention were prepared in a similar manner (scheme 3).

| Example No. | Structure | IUPAC Name | LCMS m/z |
|---|---|---|---|
| 14. | ![structure] | N-cyclopropyl-2-(4-(3-fluorophenyl)-7-hydroxy-1-oxophthalazin-2(1H)-yl)-N-(2-methylbenzo[d]oxazol-6-yl)acetamide | 485 [M + H] |

| Example No. | Structure | IUPAC Name | LCMS m/z |
|---|---|---|---|
| 15. | 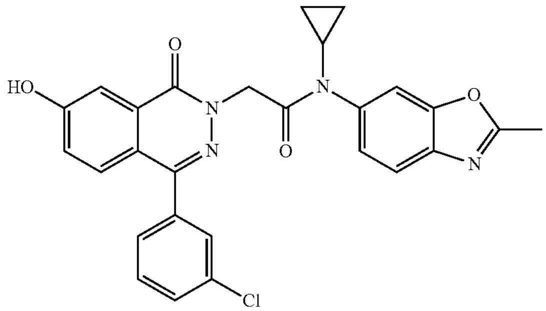 [SMILES: Cc1nc2ccc(N(C(=O)Cn3nc(-c4cccc(Cl)c4)c4ccc(O)cc4c3=O)C3CC3)cc2o1] | 2-(4-(3-chlorophenyl)-7-hydroxy-1-oxophthalazin-2(1H)-yl)-N-cyclopropyl-N-(2-methylbenzo[d]oxazol-6-yl)acetamide | 502 [M + H] |
| 16. | 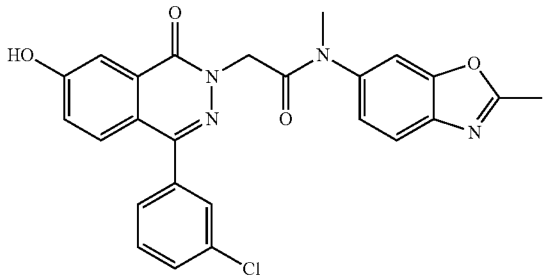 | 2-(4-(3-chlorophenyl)-7-hydroxy-1-oxophthalazin-2(1H)-yl)-N-methyl-N-(2-methylbenzo[d]oxazol-6-yl)acetamide | 476 [M + H] |

Example 17: Synthesis of 2-(7-ethoxy-4-(3-fluorophenyl)-1-oxophthalazin-2(1H)-yl)-N-methyl-N-(2-methylbenzo[d]oxazol-6-yl)acetamide

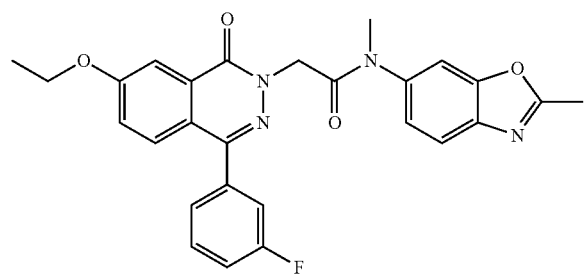

2-(4-(3-fluorophenyl)-7-hydroxy-1-oxophthalazin-2(1H)-yl)-N-methyl-N-(2-methylbenzo[d]oxazol-6-yl)acetamide (6.5 g, 14.19 mmol) was dissolved in DMF (60 mL), treated with $K_2CO_3$ (3.04 g, 21.2 mmol) and stirred at rt for 30 min. After cooling to 0° C., EtI (1.26 mL, 15.59 mmol) was added dropwise and the reaction was warmed to rt for 1 h. It was diluted with water (20 mL) and extracted with EtOAc (2×15 mL). The organics were washed with brine (300 mL), dried over $Na_2SO_4$, and concentrated to give crude material which was purified by chromatography (40% EtOAc/hexane) to yield 2-(7-ethoxy-4-(3-fluorophenyl)-1-oxophthalazin-2(1H)-yl)-N-methyl-N-(2-methylbenzo[d]oxazol-6-yl)acetamide (3.5 g) (487.52 [M+H]). $^1$H NMR: (400 MHz, DMSO) δ: 1.39-1.42 (t, 3H), 2.62 (s, 3H), 3.24 (s, 3H), 4.22-4.24 (d, J=7.2, 2H), 4.72 (s, 2H), 7.37-7.49 (m, 5H), 7.58-7.65 (m, 3H), 7.71-7.73 (d, J=8.4, 1H), 7.90 (s, 1H).

Representative compounds of the invention were prepared in a similar manner (scheme 3).

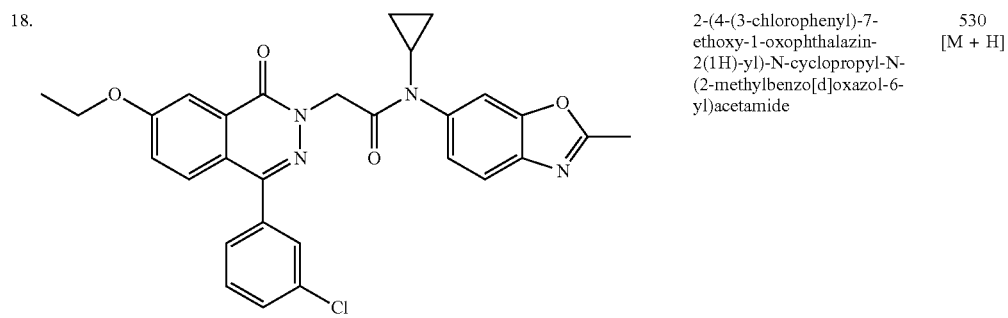

| Example No. | Structure | IUPAC Name | LCMS m/z |
|---|---|---|---|
| 18. | 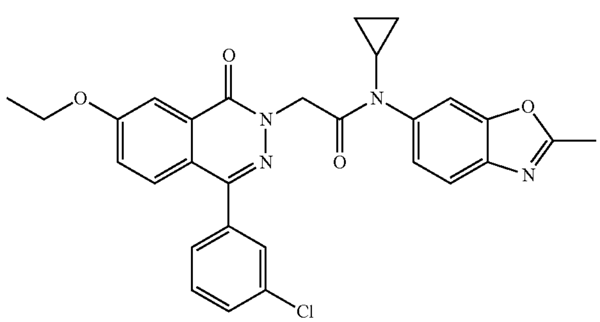 | 2-(4-(3-chlorophenyl)-7-ethoxy-1-oxophthalazin-2(1H)-yl)-N-cyclopropyl-N-(2-methylbenzo[d]oxazol-6-yl)acetamide | 530 [M + H] |

-continued

| | | | |
|---|---|---|---|
| 19. | | 2-(4-(3-chlorophenyl)-7-ethoxy-1-oxophthalazin-2(1H)-yl)-N-methyl-N-(2-methylbenzo[d]oxazol-6-yl)acetamide | 504 [M + H] |
| 20. | | 2-(4-(3-chlorophenyl)-7-isopropoxy-1-oxophthalazin-2(1H)-yl)-N-(methyl-d3)-N-(2-methylbenzo[d]oxazol-6-yl)acetamide | 521 [M + H] |
| 21. | | N-cyclopropyl-2-(7-ethoxy-4-(3-fluorophenyl)-1-oxophthalazin-2(1H)-yl)-N-(2-methylbenzo[d]oxazol-6-yl)acetamide | 514 [M + H] |
| 22. | | 2-(7-ethoxy-4-(3-fluorophenyl)-1-oxophthalazin-2(1H)-yl)-N-(methyl-d3)-N-(2-methylbenzo[d]oxazol-6-yl)acetamide | 491 [M + H] |
| 23. | | 2-(4-(3-chlorophenyl)-7-(cyclopropylmethoxy)-1-oxophthalazin-2(1H)-yl)-N-(methyl-d3)-N-(2-methylbenzo[d]oxazol-6-yl)acetamide | 533 [M + H] |

| # | Structure | Name | MS |
|---|---|---|---|
| 24. | 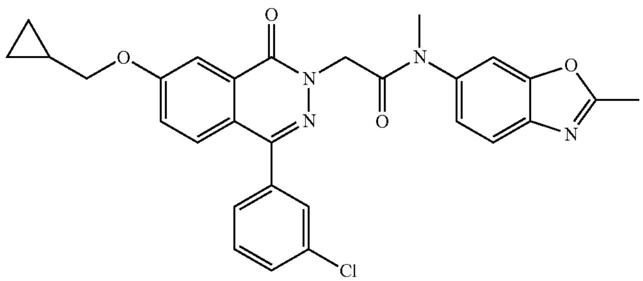 [SMILES: Cc1nc2ccc(N(C)C(=O)Cn3nc(-c4cccc(Cl)c4)c4ccc(OCC5CC5)cc4c3=O)cc2o1] | 2-(4-(3-chlorophenyl)-7-(cyclopropylmethoxy)-1-oxophthalazin-2(1H)-yl)-N-methyl-N-(2-methylbenzo[d]oxazol-6-yl)acetamide | 530 [M + H] |
| 25. | 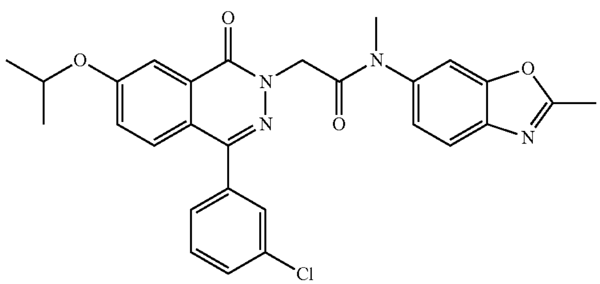 [SMILES: Cc1nc2ccc(N(C)C(=O)Cn3nc(-c4cccc(Cl)c4)c4ccc(OC(C)C)cc4c3=O)cc2o1] | 2-(4-(3-chlorophenyl)-7-isopropoxy-1-oxophthalazin-2(1H)-yl)-N-methyl-N-(2-methylbenzo[d]oxazol-6-yl)acetamide | 518 [M + H] |
| 26. | 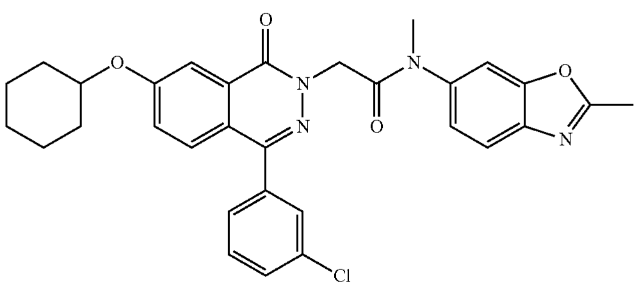 | 2-(4-(3-chlorophenyl)-7-(cyclohexyloxy)-1-oxophthalazin-2(1H)-yl)-N-methyl-N-(2-methylbenzo[d]oxazol-6-yl)acetamide | 558 [M + H] |
| 27. | 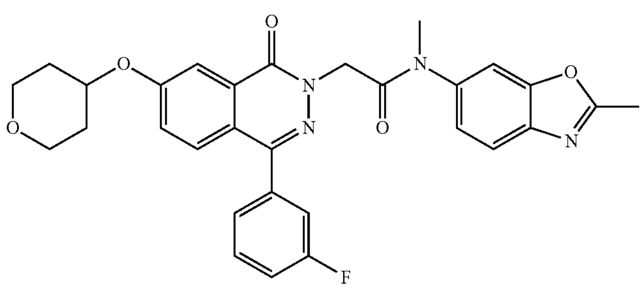 [SMILES: Cc1nc2ccc(N(C)C(=O)Cn3nc(-c4cccc(F)c4)c4ccc(OC5CCOCC5)cc4c3=O)cc2o1] | 2-(4-(3-fluorophenyl)-1-oxo-7-((tetrahydro-2H-pyran-4-yl)oxy)phthalazin-2(1H)-yl)-N-methyl-N-(2-methylbenzo[d]oxazol-6-yl)acetamide | 544 [M + H] |
| 28. | 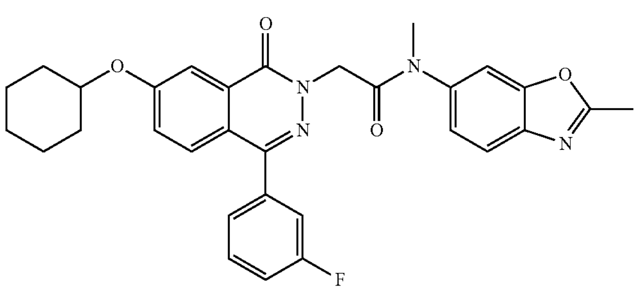 [SMILES: Cc1nc2ccc(N(C)C(=O)Cn3nc(-c4cccc(F)c4)c4ccc(OC5CCCCC5)cc4c3=O)cc2o1] | 2-(7-(cyclohexyloxy)-4-(3-fluorophenyl)-1-oxophthalazin-2(1H)-yl)-N-methyl-N-(2-methylbenzo[d]oxazol-6-yl)acetamide | 542 [M + H] |

| No. | Structure | Name | MS |
|---|---|---|---|
| 29. | 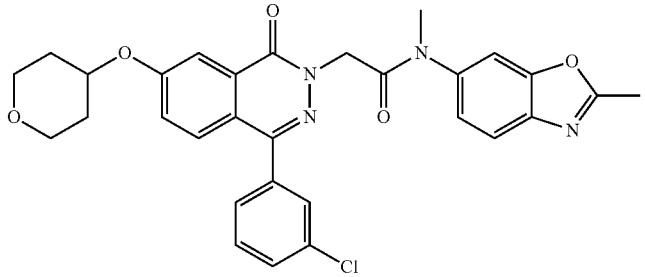 [SMILES: Cc1nc2ccc(N(C)C(=O)Cn3nc(-c4cccc(Cl)c4)c4ccc(OC5CCOCC5)cc4c3=O)cc2o1] | 2-(4-(3-chlorophenyl)-1-oxo-7-((tetrahydro-2H-pyran-4-yl)oxy)phthalazin-2(1H)-yl)-N-methyl-N-(2-methylbenzo[d]oxazol-6-yl)acetamide | 560 [M + H] |
| 30. | 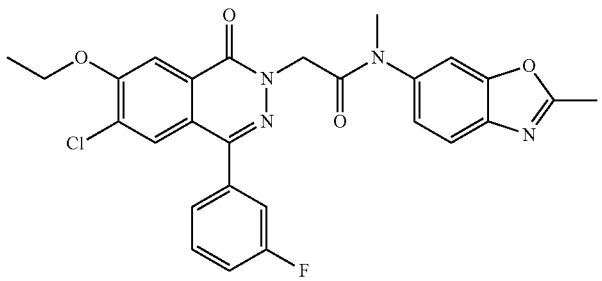 | 2-(6-chloro-7-ethoxy-4-(3-fluorophenyl)-1-oxophthalazin-2(1H)-yl)-N-methyl-N-(2-methylbenzo[d]oxazol-6-yl)acetamide | 508 [M + H] |
| 31. | 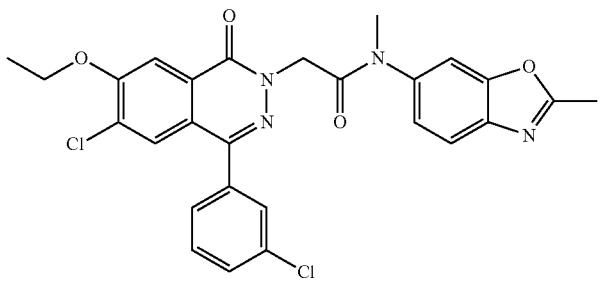 | 2-(6-chloro-4-(3-chlorophenyl)-7-ethoxy-1-oxophthalazin-2(1H)-yl)-N-methyl-N-(2-methylbenzo[d]oxazol-6-yl)acetamide | 538 [M + H] |

Assays for Detecting and Measuring the Effect of Compounds on F508del-CFTR Channels CFTR-YFP Assay-CFTR Corrector Protocol:

This protocol is designed to selectively screen small molecule compounds for F508del CFTR corrector activities in the YFP (yellow fluorescent protein) flux assay. In this protocol, the cells are incubated with testing compounds for 24 hours, washed with PBS, stimulated with forskolin and a standard potentiator, and fluorescence in each plate well is measured kinetically read on a 384-well plate reader, such as the Hamamatsu FDSS-6000.

YFP fluorescence intensity values are acquired at high speed before and after iodide buffer is injected to the assay cells. Iodide enters the cells via active CFTR channels in the plasma membrane, and quenches the YFP fluorescence. The rate of fluorescence quenching is proportionate to the total CFTR activity in the cell membrane. F508del CFTR correctors increase the number of CFTR molecules in the testing cell plasma membrane, and thereby accelerate YFP quenching.

This method was initially developed for bench top plate readers (Galietta, J, Jayaraman, S and Verkman, A S. Cell-based assay for high-throughput quantitative screening of CFTR chloride transport agonists. Am. J. Physiol. Cell Physiol. (2001), 281: C173), and was adapted to the HTS format (Sui J, Cotard S, Andersen J, Zhu P, Staunton J, Lee M, Lin S. Optimization of a Yellow fluorescent protein-based iodide influx high-throughput screening assay for cystic fibrosis transmembrane conductance regulator (CFTR) modulators. Assay Drug Dev Technol. (2010), 8: 656-668).

Fisher Rat Thyroid (FRT) cells stably expressing both human F508del CFTR and a halide-sensitive yellow fluorescent protein (YFP-H148Q/I152L 25, 22) (Galietta et al. Am. J. Physiol Cell Physiol 281(5), C1734, 2001) were cultured on plastic surface in Coon's modified Ham's F12 medium supplemented with FBS 10%, L-glutamine 2 mM, penicillin 100 U/ml, and streptomycin 100 µg/ml. G418 (0.75-1.0 mg/ml) and zeocin (3.2 ug/ml) were used for selection of FRT cells expressing F508del CFTR and YFP. For primary screening, FRT cells were plated into 384-well black wall, transparent bottom microtiter plates (Costar; Corning Inc.) at a cell density of 20,000-40,000 per well. Test compound was applied to the cells at varying concentrations ranging from 2 nM-40 µM in either a 2-fold or 3-fold dilution series. Cells were incubated in a cell culture incubator at 37° C. with 5% $CO_2$ for 24-26 h. Assay plates were washed with DPBS media (Thermo, cat# SH30028.02) to remove unbound cells and compound. Stimulation media (25 µL) containing 20 µM Forskolin & 30 µM P3 [6-(Ethyl-phenyl-sulfonyl)-4-oxo-1,4-dihydro-quinoline-3-carboxylic acid 2-methoxy-benzylamide] in Hams F-12 coon's modified media was added to the plate wells and incubated at room temperature for 60-120 min. 25 µL of HEPES-PBS-I buffer (10 mM HEPES, 1 mM $MgCl_2$, 3 mM KCl, 1 mM $CaCl_2$), 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data as described by Sui et al (2010).

CFTR-YFP Assay-CFTR Potentiator Protocol:

This protocol is designed to selectively screen small molecule compounds for F508del CFTR potentiator activities in the YFP (yellow fluorescent protein) flux assay. Such compounds act acutely to stimulate CFTR already expressed on the membrane surface. In this protocol, the cells are incubated at 27° C. for 24 hours to homogeneously boost F508del CFTR expression in the cell membrane (low temperature correction), washed with PBS, treated with test compound, and CFTR activity is stimulated with forskolin for 1-2 hr. Measurement of ion flux is initiated by addition of iodide-containing buffer, and YFP quenching is kinetically recorded using a 384-well plate reader, such as the Hamamatsu FDSS-6000.

YFP fluorescence intensity values are acquired at high speed over a 1 min time course before and after iodide buffer is injected to the assay cells. Iodide enters the cells via active CFTR channels in the plasma membrane, and quenches the YFP fluorescence. The rate of fluorescence quenching is proportionate to total CFTR activity in the cell membrane. F508del-CFTR potentiators increase CFTR open probability or CFTR-mediated ion conductivity, and this enhanced CFTR mediated iodide flux in the test cell plasma membrane accelerates YFP quenching.

This method was initially developed for bench top plate readers (Galietta, J, Jayaraman, S and Verkman, A S. Cell-based assay for high-throughput quantitative screening of CFTR chloride transport agonists. Am. J. Physiol Cell Physiol (2001), 281: C1734), and was adapted to the HTS format (Sui J, Cotard S, Andersen J, Zhu P, Staunton J, Lee M, Lin S. Optimization of a Yellow fluorescent protein-based iodide influx high-throughput screening assay for cystic fibrosis transmembrane conductance regulator (CFTR) modulators. Assay Drug Dev Technol. (2010), 8: 656-668).

Fisher Rat Thyroid (FRT) cells stably expressing both human F508del CFTR and a halide-sensitive yellow fluorescent protein (YFP-H148Q/I152L 25, 22) (Galietta et al., Am. J. Physiol Cell Physiol 281(5), C1734, 2001) were cultured on plastic surface in Coon's modified Ham's F12 medium supplemented with FBS 10%, L-glutamine 2 mM, penicillin 100 U/ml, and streptomycin 100 μg/ml. G418 (0.75-1.0 mg/ml) and zeocin (3.2 ug/ml) were used for selection of FRT cells expressing F508del CFTR and YFP. For primary screening, FRT cells were plated into 384-well black wall, transparent bottom microtiter plates (Costar; Corning Inc.) at a cell density of 20,000-40,000 per well. Cells were incubated in a cell culture incubator at 37° C. with 5% $CO_2$ for 24-26 h. Assay plates were washed with DPBS media (Thermo, cat# SH30028.02) to remove unbound cells. Test compound was applied to the cells at varying concentrations ranging from 2 nM-40 μM in either a 2-fold or 3-fold dilution series in DPBS and stimulated with 20 μM Forskolin (final concentration) in Hams F-12 coon's modified media. Plates were incubated at room temperature for 60-120 min. 25 μL of HEPES-PBS-I buffer (10 mM HEPES, 1 mM $MgCl_2$, 3 mM KCl, 1 mM $CaCl_2$, 150 mM NaI) was then added and fluorescence quench curves (Excitation 500 nm/Emission 540 nm; exposure 136 ms) were immediately recorded on an FDSS-6000 plate reader (Hamamatsu). Quench rates were derived from least squares fitting of the data as described by Sui et al (2010).

Cell Culture:

Primary CF airway epithelial cells were obtained from the UNC Cystic Fibrosis Tissue Procurement and Cell Culture Core. The cells are grown at 37° C. in a Heracell 150i incubator using growth media (BEGM, Fischer). Cells were then transferred to differentiation media (ALI, UNC) for a minimum of 4 weeks on coated Costar snapwells. Two days before the Ussing assay the mucus on the apical surface of the cells was aspirated after incubating with 200 μL of differentiation Media for at least thirty (30) minutes. One day before the Ussing assay, test compounds were applied to the basolateral surface of the cells at various test concentrations (n=3 or n=4 replicates per test condition).

Ussing Assay

Ussing chambers and the associated voltage clamp were obtained from Physiologic Instruments, (San Diego, Calif.). Ussing assays were performed at the 37° C. HEPES buffered physiological saline (HB-PS) was used in apical and basolateral chambers with glucose added to the basolateral solutions. Epithelia were equilibrated for 15 minutes in the chambers while the bath temperature and transepithelial voltage were stabilized and adjusted before application of voltage clamp.

Compounds were added in the following order.

| Step | Chamber |
|---|---|
| 3.0 uM Benzamil for 20 minutes | apical addition only |
| 10 uM Forskolin for 20 minutes | apical + basolateral addition |
| 10 uM Genestein for 20 minutes | apical + basolateral addition |
| 10 uM CFTR-172 for 20 minutes | apical + basolateral addition |
| 20 uM Bumetanide for 30 minutes | basolateral addition only |

The short circuit current and transepithelial resistances (typically >300 Ω-cm2) from each chamber was recorded every 10 seconds on stored on a PC using Acquire and Analyze (Physiologic Instruments).

Analysis

Efficacy of test compounds was compared using the average of the forskolin response and the CFTR-172 inhibited current response of the test compound divided by the average of the forskolin response and the CFTR-172 inhibited current elicited by the positive control. Normalized scores were tabulated for all compounds and concentrations.

TABLE I

CFTR-YFP High Throughput Assay; The following meanings apply: % Efficacy is reported as the EMax normalized to the positive control. "+++" refers to EMax >80%, "++" refers to a range of 80%-30%, "+" refers to a range of 30%-10%. $EC_{50}$: "+++" refers to $EC_{50}$ <10 μM, "++" refers to $EC_{50}$ range of between 10-20 μM, "+" refers to $EC_{50}$ >20 μM.

| Example | % Efficacy | $EC_{50}$ |
|---|---|---|
| 1. | +++ | +++ |
| 2. | ++ | +++ |
| 3. | ++ | +++ |
| 4. | +++ | +++ |
| 5. | +++ | +++ |
| 6. | +++ | +++ |
| 7. | +++ | +++ |
| 8. | +++ | +++ |
| 9. | +++ | +++ |
| 10. | ++ | +++ |
| 11. | +++ | +++ |
| 12. | +++ | +++ |
| 13. | +++ | +++ |
| 14. | ++ | +++ |
| 15. | +++ | +++ |
| 16. | +++ | +++ |
| 17. | +++ | +++ |
| 18. | +++ | +++ |
| 19. | +++ | +++ |
| 20. | ++ | +++ |
| 21. | +++ | +++ |

TABLE I-continued

CFTR-YFP High Throughput Assay; The following meanings apply:
% Efficacy is reported as the EMax normalized to the positive
control. "+++" refers to EMax >80%, "++" refers
to a range of 80%-30%, "+" refers to a range of 30%-10%.
$EC_{50}$: "+++" refers to $EC_{50}$ <10 µM, "++" refers to
$EC_{50}$ range of between 10-20 µM, "+" refers to $EC_{50}$ >20 µM.

| Example | % Efficacy | $EC_{50}$ |
|---|---|---|
| 22. | +++ | +++ |
| 23. | ++ | +++ |
| 24. | +++ | +++ |
| 25. | +++ | +++ |
| 26. | +++ | +++ |
| 27. | +++ | +++ |
| 28. | +++ | +++ |
| 29. | +++ | +++ |
| 30. | ++ | +++ |
| 31. | +++ | +++ |

While this invention has been particularly shown and described with references to preferred embodiments thereof, it will be understood by those skilled in the art that various changes in form and details may be made therein without departing from the scope of the invention encompassed by the appended claims.

What is claimed:

1. A compound of Formula IA:

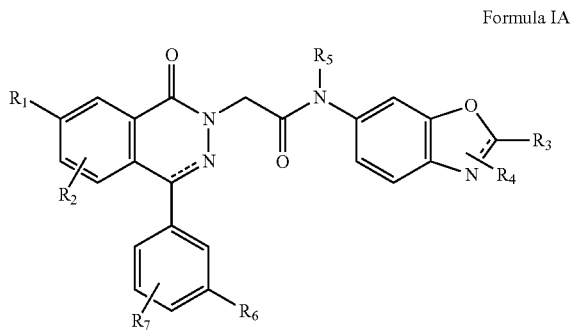

Formula IA or a pharmaceutically acceptable salt, ester or prodrug thereof;
wherein ═══ represents a double bond;
$R_1$ is —$C_1$-$C_8$ alkoxy;
$R_2$ is hydrogen;
$R_3$ is methyl;
$R_4$ is absent;
$R_5$ is selected from $C_1$-$C_8$ alkyl and $C_3$-$C_6$-cycloalkyl;
$R_6$ is halogen; and,
$R_7$ is selected from hydrogen or halogen.

2. A pharmaceutical composition comprising a compound according to claim 1, and a pharmaceutically acceptable carrier.

3. A method of treating a disease or disorder mediated by cystic fibrosis transmembrane conductance regulator (CFTR) in a subject in need thereof, comprising the step of administering to the subject a therapeutically effective amount of a compound according to claim 1.

4. The method according to claim 3, wherein said disease or disorder is selected from cystic fibrosis, hereditary emphysema, hereditary hemochromatosis, coagulation-fibrinolysis deficiencies, type 1 hereditary angioedema, lipid processing deficiencies, such as familial hypercholesterolemia, type 1 chylomicronemia, abetalipoproteinemia, lysosomal storage diseases, such as I-cell disease/pseudo Hurler, mucopolysaccharidoses, Sandhof/Tay-Sachs, Crigler-Najjar type II, polyendocrinopathy/hyperinsulemia, diabetes mellitus, Laron dwarfism, myeloperoxidase deficiency, primary hypoparathyroidism, melanoma, glycanosis CDG type 1, congenital hyperthyroidism, osteogenesis imperfecta, hereditary hypofibrinogenemia, ACT deficiency, diabetes insipidus (DI), neurophyseal DI, neprogenic DI, Charcot-Marie tooth syndrome, Perlizaeus-Merzbacher disease, neurodegenerative diseases such as Alzheimer's disease, Parkinson's disease, amyotrophic lateral sclerosis, progressive supranuclear palsy, Pick's disease, several polyglutamine neurological disorders disorders such as Huntington's disease, Spinocerebullar ataxia type I, Spinal and bulbar muscular atrophy, Dentororubal pallidoluysian, and Myotic dystrophy, as well as, spongiform encephalopathies such as Hereditary Creutzfeldt-Jakob disease, Fabry disease, Straussler-Scheinker disease, secretory diarrhea, polycystic kidney disease, chronic obstructive pulmonary disease (COPD), dry eye disease, or Sjogren's Syndrome.

5. A method for treating cystic fibrosis or a symptom thereof in a subject in need thereof, comprising the step of administering to the subject a therapeutically effective amount of a compound according to claim 1.

6. A composition comprising a compound according to claim 1 and a compound selected from Gentamicin, Ataluren, Ivacaftor (Kalydeco) and VX-809.

* * * * *